United States Patent
Kensey et al.

(10) Patent No.: US 6,624,435 B2
(45) Date of Patent: Sep. 23, 2003

(54) DUAL RISER/DUAL CAPILLARY VISCOMETER FOR NEWTONIAN AND NON-NEWTONIAN FLUIDS

(75) Inventors: Kenneth Kensey, Malvern, PA (US); William N. Hogenauer, Gilbertsville, PA (US); John E. Nash, Chester Springs, PA (US); Harold E. Clupper, West Chester, PA (US); Sangho Kim, Philadelphia, PA (US); Young Cho, Cherry Hill, NJ (US); Peter Randolph Hazard Stark, Andover, MA (US); Roberto O. Pellizzari, Groton, PA (US); Sergey Kruss, Millis, MA (US)

(73) Assignee: Rheologics, Inc., Exton, PA (US)

( * ) Notice: Subject to any disclaimer, the term of this patent is extended or adjusted under 35 U.S.C. 154(b) by 96 days.

(21) Appl. No.: 10/033,841

(22) Filed: Dec. 27, 2001

(65) Prior Publication Data

US 2002/0088953 A1 Jul. 11, 2002

Related U.S. Application Data

(60) Division of application No. 09/615,340, filed on Jul. 12, 2000, now Pat. No. 6,428,488, which is a continuation-in-part of application No. 09/439,795, filed on Nov. 12, 1999, now Pat. No. 6,322,524, which is a continuation-in-part of application No. 08/919,906, filed on Aug. 28, 1997, now Pat. No. 6,019,735.

(51) Int. Cl.[7] ............................................. G01N 15/06
(52) U.S. Cl. ...................................... 250/577; 250/576
(58) Field of Search ......................... 250/577, 573–576, 250/578.1, 221; 73/1 H, 54.01, 290 R, 293; 340/450, 619; 356/437

(56) References Cited

U.S. PATENT DOCUMENTS

| | | |
|---|---|---|
| 1,810,992 A | 6/1931 | Dallwitz-Wegner |
| 2,343,061 A | 2/1944 | Irany |
| 2,696,734 A | 12/1954 | Brunstrum et al. |
| 2,700,891 A | 2/1955 | Shafer |

(List continued on next page.)

FOREIGN PATENT DOCUMENTS

| | | |
|---|---|---|
| DE | 31 38514 A1 | 4/1983 |
| EP | 0 654 286 A1 | 12/1994 |
| FR | 2 510 257 | 1/1983 |
| WO | WO 92/15878 | 9/1992 |
| WO | WO 94/20832 | 9/1994 |
| WO | WO 99/10724 | 3/1999 |

OTHER PUBLICATIONS

Ernst, et al., Cardiovascular Risk Factors & Hemorrheolgoy: Physical Fitness, Stress & Obesity, Atheros. V. 59, 263–269, 1986. (Month unknown).

(List continued on next page.)

*Primary Examiner*—Que T. Le
(74) *Attorney, Agent, or Firm*—Caesar, Rivise, Bernstein, Cohen & Pokotilow, Ltd.

(57) ABSTRACT

An apparatus and method for measuring the viscosity of Newtonian and non-Newtonian fluids over a range of shear rates, especially low shear rates, by monitoring two rising columns of fluid (Newtonian or non-Newtonian) that pass through respective capillaries having different lengths. Furthermore, a specialized column monitor is provided that uses multiple interrogation sources (e.g., lasers) and a single detector (e.g., a charge-coupled device (CCD) array) to continuously monitor both columns of fluid substantially simultaneously. In particular, the system includes a Y-connector to form two flow paths and wherein each flow path includes a tube that includes a riser tube, a capillary tube of predetermined dimensions and a valve in each for controlling the fluid flow in each path. The specialized column monitor monitors the movement of the fluid columns in each of the riser tubes and an associated microprocessor analyzes these movements, along with the predetermined dimensions of the capillary tubes and riser tubes to determine the viscosity of the fluid.

16 Claims, 16 Drawing Sheets

U.S. PATENT DOCUMENTS

| | | |
|---|---|---|
| 2,934,944 A | 5/1960 | Eolkin |
| 3,071,961 A | 1/1963 | Heigl et al. |
| 3,116,630 A | 1/1964 | Piros |
| 3,137,161 A | 6/1964 | Lewis et al. |
| 3,138,950 A | 6/1964 | Welty et al. |
| 3,277,694 A | 10/1966 | Cannon et al. |
| 3,286,511 A | 11/1966 | Harkness |
| 3,342,063 A | 9/1967 | Smythe et al. |
| 3,435,665 A | 4/1969 | Tzentis |
| 3,520,179 A | 7/1970 | Reed |
| 3,604,247 A | 9/1971 | Gramain et al. |
| 3,666,999 A | 5/1972 | Moreland, Jr. et al. |
| 3,680,362 A | 8/1972 | Geerdes et al. |
| 3,699,804 A | 10/1972 | Gassmann et al. |
| 3,713,328 A | 1/1973 | Aritomi |
| 3,720,097 A | 3/1973 | Kron |
| 3,782,173 A | 1/1974 | Van Vessem et al. |
| 3,839,901 A | 10/1974 | Finkle et al. |
| 3,853,121 A | 12/1974 | Mizrachy et al. |
| 3,864,962 A | 2/1975 | Stark et al. |
| 3,908,441 A | 9/1975 | Virloget |
| 3,911,728 A | 10/1975 | Fixot |
| 3,952,577 A | 4/1976 | Hayes et al. |
| 3,967,934 A | 7/1976 | Seitz et al. |
| 3,990,295 A | 11/1976 | Renovanz et al. |
| 3,999,538 A | 12/1976 | Philpot, Jr. |
| 4,083,363 A | 4/1978 | Philpot, Jr. |
| 4,149,405 A | 4/1979 | Ringrose |
| 4,165,632 A | 8/1979 | Weber et al. |
| 4,193,293 A | 3/1980 | Cavallari |
| 4,207,870 A | 6/1980 | Eldridge |
| 4,302,965 A | 12/1981 | Johnson et al. |
| 4,341,111 A | 7/1982 | Husar |
| 4,417,584 A | 11/1983 | Cathignol et al. |
| 4,426,878 A | 1/1984 | Price et al. |
| 4,432,761 A | 2/1984 | Dawe |
| 3,999,538 | 7/1984 | Philpot, Jr. |
| 4,461,830 A | 7/1984 | Philpot, Jr. |
| 4,517,830 A | 5/1985 | Gunn et al. |
| 4,519,239 A | 5/1985 | Kiesewetter et al. |
| 4,554,821 A | 11/1985 | Kiesewetter et al. |
| H93 H | 7/1986 | Matta et al. |
| 4,616,503 A | 10/1986 | Plungis et al. |
| 4,637,250 A | 1/1987 | Irvine, Jr. et al. |
| 4,643,021 A | 2/1987 | Mattout |
| 4,680,957 A | 7/1987 | Dodd |
| 4,680,958 A | 7/1987 | Ruelle et al. |
| 4,750,351 A | 6/1988 | Ball |
| 4,856,322 A | 8/1989 | Langrick et al. |
| 4,858,127 A | 8/1989 | Kron et al. |
| 4,884,577 A | 12/1989 | Merrill |
| 4,899,575 A | 2/1990 | Chu et al. |
| 4,947,678 A | 8/1990 | Hori et al. |
| 5,099,698 A | 3/1992 | Kath et al. |
| 5,142,899 A | 9/1992 | Park et al. |
| 5,181,415 A | 1/1993 | Esvan et al. |
| 5,222,497 A | 6/1993 | Ono |
| 5,224,375 A | 7/1993 | You et al. |
| 5,257,529 A | 11/1993 | Taniguchi et al. |
| 5,271,398 A | 12/1993 | Schlain et al. |
| 5,272,912 A | 12/1993 | Katsuzaki |
| 5,327,778 A | 7/1994 | Park |
| 5,333,497 A | 8/1994 | Br nd Dag A. et al. |
| 5,365,776 A | 11/1994 | Lehmann et al. |
| 5,421,328 A | 6/1995 | Bedingham |
| 5,447,440 A | 9/1995 | Davis et al. |
| 5,491,408 A | 2/1996 | Rousseau |
| 5,494,639 A | 2/1996 | Grzegorzewski |
| 5,629,209 A | 5/1997 | Braun, Sr. et al. |
| 5,686,659 A | 11/1997 | Neel et al. |
| 5,725,563 A | 3/1998 | Klotz |
| 5,792,660 A | 8/1998 | Spillert et al. |
| 5,837,885 A | 11/1998 | Goodbread et al. |
| 6,019,735 A | 2/2000 | Kensey et al. |
| 6,039,078 A | 3/2000 | Tamari |
| 6,077,234 A | 6/2000 | Kensey |
| 6,152,888 A | 11/2000 | Kensey et al. |
| 6,193,667 B1 | 2/2001 | Kensey |
| 6,200,277 B1 | 3/2001 | Kensey |
| 6,261,244 B1 | 7/2001 | Kensey et al. |
| 6,322,524 B1 | 11/2001 | Kensey et al. |
| 6,322,525 B1 | 11/2001 | Kensey et al. |
| 6,402,703 B1 | 6/2002 | Kensey et al. |
| 6,448,574 B1 * | 9/2002 | Chow ............... 250/577 |

OTHER PUBLICATIONS

Levenson, et al., Cigarette Smoking & Hypertension, Atherosclerosis V. 7, 572–577, 1987 (Month unknown).

Rillaerts, et al., Blood viscosity in Human Obesity; relation to glucose Tolerance and Insulin Status, Internl Jnl. Of Obesity, V. 13, 739–741, 1989. (Month unknown).

Rosenson, R., Viscosity & Ischemic Heart Disease, Jnl. Of Vascular Medicine & Biol., V. 4, 206–212, 1993 (Month unknown).

Letcher, et al., Direct Relationship Between Blood Pressure & Blood Viscosity in Normal & Hypertensive Subjects, Am. Jnl of Med. V. 70, 1195–1203, Jun. 1981.

Zwick, K.J., The Fluid Mechanics of Bonding with Yield Stress Exposies, Dissertation, Un. Of Penn., PA, USA, 1–142, 1996 (Month unknown).

Yarnell, et al., Fibrinogen, viscosity & White Blood Cell Count are Major Risk Factors for Ischemic Heart Disease, Circulation, V. 83, No. 3, Mar. 1991.

Tangney, et al., Postprandial changes in Plasma & Serum Viscosity & Plasma Lipids & Lipoproteins after an acute test meal, Am. Jnl. Of Clin. Nutrition V. 65, 36–40, 1997 (Month unknown).

Seplowitz, et al., Effects of Lipoproteins on Plasma Viscosity, Atherosclerosis, V. 38, 89–95, 1981 (Month unknown).

Rosenson, et al., Hyperviscosity Syndrome in Hyperchloesterolemic Patient with Primary Biliary Cirrhosis, Gastroenterology, V. 98, No. 5, 1990 (Month unknown).

Lowe, et al., Blood Viscosity & Risk of Cardiovascular Events: the Edinburgh Artery Study, British Jnl. Of Haematology, V. 96, 168–173, 1997 (Month unknown).

Koenig, W., Blood Rheology Assoc. with Cardiovascular Risk Factors & Chronic Cardiovascular Diseases: Results of an Epidemiologic Cross Sectional Study, Am. Coll. Of Angiology, Paradise Is., Bahamas , Oct. 1997 (Month unknown).

Hell, K., Importance of Blood Viscoelasticity in Arteriosclerosis, Internl Coll. Of Angiology , Montreux, Switzerland, Jul. 1987.

Delaunois, A., Thermal method for Continuous Blood velocity Measurements in Large Blood Vessels & Cardiac Output Determination, Medical & Biological Engineering, Mar. 1973, V. 11, 201–205.

Nerem, et al., Fluid Mechanics in Atherosclerosis, Handbook of Bioengineering, Chp. 21, 20.24 to 21.22 (No date).

Litt, et al., Theory & Design of Disposable Clinical Blood Viscometer, Biorheology, V. 25, 697–712, 1988 (Month unknown).

Cooke, et al., Automated Measurement of Plasma Viscosity by Capillary Viscometer, J. Clin. Path., vol. 341, 1213–1216, 1988 (Month unknown).

Jiminez, et al., A novel computerized Viscometer/rheometer, Rev. sci. Instrum. V. 65, (1), 229–241, Jan. 1994.

Harkness, A New Instrument for Measurement of Plasma--Viscosity, Med. & Biol. Engineering, Sep. 1976.

Pringle, et al., Blood Viscosity & Raynaud's Disease, The Lancet, May 1965.

Walker, et al., Measurement of Blood Viscosity using a conicylindrical viscometer, Med. & Biol. Engineering, Sep. 1976.

Oguraa, et al., Measurement of Human Red Blood Cell Deformability using a Single Micropore on a Thin $Si_3N_4$ Film, IEEE Transactions on Biomedical Engineering, V. 38, No. 9, Aug. 1991.

Hausler, et al., A Newly Designed Oscillating Viscometer for Blood Viscosity Measurements, 1999 V. 33, No. 4, Biorheology, p. 397–404 (Month unknown).

Martin, et al., Apparent Viscosity of Whole Human Blood at Various Hydrostatic Pressure I. Studies on Anticoagulated Blood Employing new Capillary Viscometer, Biorheology 3–12, V. 11, 1978 (Month unknown).

Rheinhardt, et al., Rheologic Measuremens on Small Samples with a New Capillary Viscometer, J.Lab. And Clin. Med., 921–931, Dec. 1984.

Chmiel, A New Capillary Viscometer for Clinical use, Biorheology, 301–307, V. 12, 1979 (Month unknown).

Pall Corporation, Pall BPF4 High Efficiency Leukocyte Removal Blood Processing Filter System, Pall Biomedical Products Corporation 1993 (Month unknown).

Qamar, et al., The Goldman Algorithm Revisited: Prospective E#valuation of Computer Derived Algorithm Vs. Unaided Physician Judgement in Suspected Acute Myocardial Inf., AM. Hrt J. 138, V. 4, 705–709, 1999 (Month unknown).

Leonhart, et al., Studies of Plasma Viscosity in Primary Hyperlipoproteinaemia, Atherosclerosis, V.28, 29–40, 1977 (Month unknown).

* cited by examiner

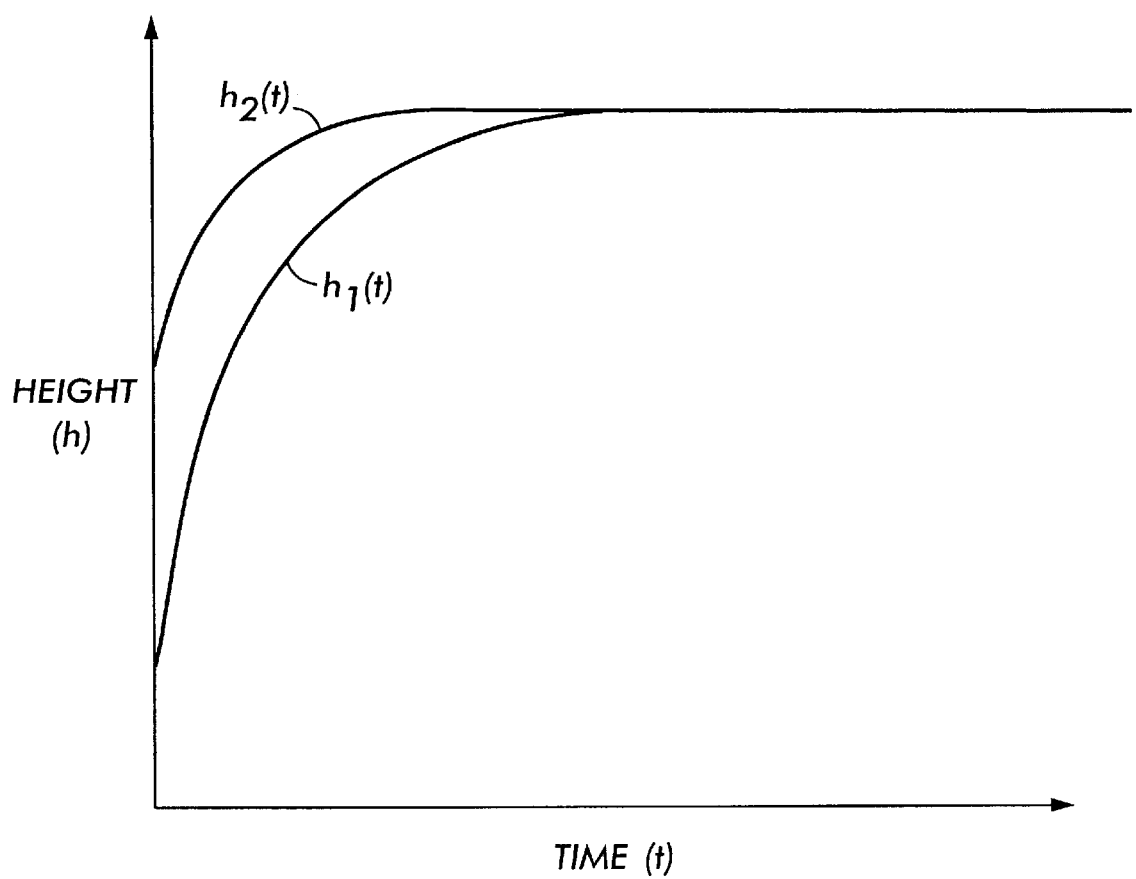

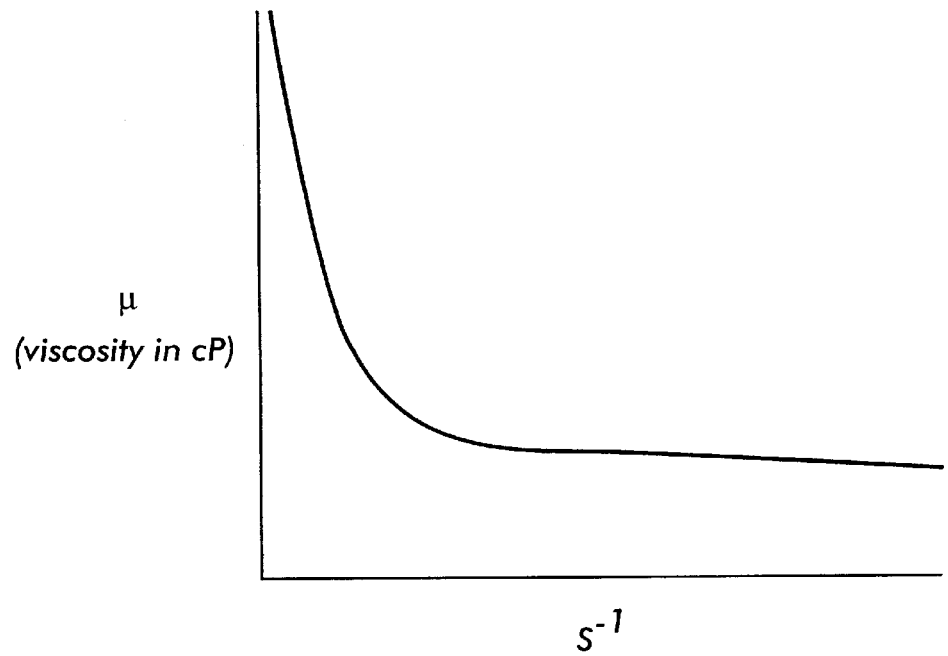
FIG.IIA
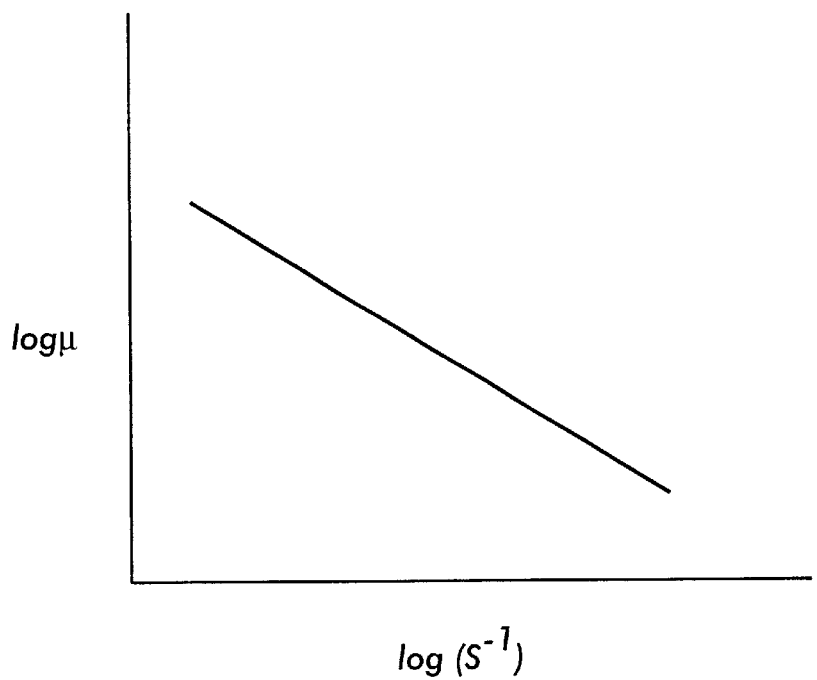
FIG.IIB

DUAL RISER/DUAL CAPILLARY VISCOMETER FOR NEWTONIAN AND NON-NEWTONIAN FLUIDS

RELATED APPLICATIONS

This application is a Divisional application of Co-Pending application Ser. No. 09/615,340, filed on Jul. 12, 2000, now U.S. Pat. No. 6,428,488, entitled DUAL RISER/DUAL CAPILLARY VISCOMETER FOR NEWTONIAN AND NON-NEWTONIAN FLUIDS, which in turn is a Continuation-in-Part of application Ser. No. 09/439,795, filed Nov. 12,1999 (now U.S. Pat. No. 6,322,524, issued on Nov. 27, 2001), entitled DUAL RISER/SINGLE CAPILLARY VISCOMETER, which in turn is a Continuation-in-Part of application Ser. No. 08/919,906, filed Aug. 28,1997 (now U.S. Pat. No. 6,019,735, issued on Feb. 1, 2000), entitled VISCOSITY MEASURING APPARATUS AND METHOD OF USE, all of which are assigned to the same Assignee as the present invention and all of whose entire disclosures are incorporated by reference herein.

BACKGROUND OF THE INVENTION

This invention relates generally to an apparatus and method for measuring the viscosity of liquids, and more particularly, an apparatus and methods for measuring the viscosity of both Newtonian fluids and non-Newtonian fluids over a wide range of shears.

Viscometers currently available may be grouped into three broad categories: 1) capillary tube viscometers; 2) rotating viscometers; and 3) falling ball or needle viscometers. Most of these techniques yield viscosity measurements at a specified, constant shear rate; for measuring Newtonian fluids, i.e., fluids where the viscosity does not vary with shear rate, these techniques are satisfactory. However, for determining the viscosity of non-Newtonian fluids, i.e., where the viscosity varies with shear rate, in order to measure the viscosity over a range of shear rates, one needs to make repetitive measurements while varying either the pressure in the reservoir tank of capillary tube viscometers, the rotating speed of the cup/cone in rotating viscometers, or the density of the falling objects. Such operations can make these viscosity-measurement techniques difficult, time consuming and labor intensive.

With particular regard to measuring the viscosity of a non-Newtonian fluid, such as blood, there are a number of patents relating to blood viscosity measuring apparatus and methods. See for example, U.S. Pat. Nos.: 3,342,063 (Smythe et al.); 3,720,097 (Kron); 3,999,538 (Philpot, Jr.); 4,083,363 (Philpot); 4,149,405 (Ringrose); 4,165,632 (Weber, et. al.); 4,517,830 (Gunn, deceased, et. al.); 4,519,239 (Kiesewetter, et. al.); 4,554,821 (Kiesewetter, et. al.); 4,858,127 (Kron, et. al.); 4,884,577 (Merrill); 4,947,678 (Hori et al.); 5,181,415 (Esvan et al.); 5,257,529 (Taniguchi et al.); 5,271,398 (Schlain et al.); and 5,447,440 (Davis, et. al.).

The Smythe '063 patent discloses an apparatus for measuring the viscosity of a blood sample based on the pressure detected in a conduit containing the blood sample. The Kron '097 patent discloses a method and apparatus for determining the blood viscosity using a flowmeter, a pressure source and a pressure transducer. The Philpot '538 patent discloses a method of determining blood viscosity by withdrawing blood from the vein at a constant pressure for a predetermined time period and from the volume of blood withdrawn. The Philpot '363 patent discloses an apparatus for determining blood viscosity using a hollow needle, a means for withdrawing and collecting blood from the vein via the hollow needle, a negative pressure measuring device and a timing device. The Ringrose '405 patent discloses a method for measuring the viscosity of blood by placing a sample of it on a support and directing a beam of light through the sample and then detecting the reflected light while vibrating the support at a given frequency and amplitude. The Weber '632 patent discloses a method and apparatus for determining the fluidity of blood by drawing the blood through a capillary tube measuring cell into a reservoir and then returning the blood back through the tube at a constant flow velocity and with the pressure difference between the ends of the capillary tube being directly related to the blood viscosity. The Gunn '830 patent discloses an apparatus for determining blood viscosity that utilizes a transparent hollow tube, a needle at one end, a plunger at the other end for creating a vacuum to extract a predetermined amount and an apertured weight member that is movable within the tube and is movable by gravity at a rate that is a function of the viscosity of the blood. The Kiesewetter '239 patent discloses an apparatus for determining the flow shear stress of suspensions, principally blood, using a measuring chamber comprised of a passage configuration that simulates the natural microcirculation of capillary passages in a being. The Kiesewetter '821 patent discloses another apparatus for determining the viscosity of fluids, particularly blood, that includes the use of two parallel branches of a flow loop in combination with a flow rate measuring device for measuring the flow in one of the branches for determining the blood viscosity. The Kron '127 patent discloses an apparatus and method for determining blood viscosity of a blood sample over a wide range of shear rates. The Merrill '577 patent discloses an apparatus and method for determining the blood viscosity of a blood sample using a hollow column in fluid communication with a chamber containing a porous bed and means for measuring the blood flow rate within the column. The Hori '678 patent discloses a method for measurement of the viscosity change in blood by disposing a temperature sensor in the blood flow and stimulating the blood so as to cause a viscosity change. The Esvan '415 patent discloses an apparatus that detects the change in viscosity of a blood sample based on the relative slip of a drive element and a driven element, which holds the blood sample, that are rotated. The Taniguchi '529 patent discloses a method and apparatus for determining the viscosity of liquids, e.g., a blood sample, utilizing a pair of vertically-aligned tubes coupled together via fine tubes while using a pressure sensor to measure the change of an internal tube pressure with the passage of time and the change of flow rate of the blood. The Bedingham '328 patent discloses an intravascular blood parameter sensing system that uses a catheter and probe having a plurality of sensors (e.g., an $O_2$ sensor, $CO_2$ sensor, etc.) for measuring particular blood parameters in vivo. The Schlain '398 patent discloses a intra-vessel method and apparatus for detecting undesirable wall effect on blood parameter sensors and for moving such sensors to reduce or eliminate the wall effect. The Davis '440 patent discloses an apparatus for conducting a variety of assays that are responsive to a change in the viscosity of a sample fluid, e.g., blood.

Viscosity measuring devices and methods for fluids in general are well-known. See for example, U.S. Pat. Nos.: 1,810,992 (Dallwitz-Wegner); 2,343,061 (Irany); 2,696,734 (Brunstrum et al.); 2,700,891 (Shafer); 2,934,944 (Eolkin); 3,071,961 (Heigl et al.); 3,116,630 (Piros); 3,137,161 (Lewis et al.); 3,138,950 (Welty et al.); 3,277,694 (Cannon et al.); 3,286,511 (Harkness); 3,435,665 (Tzentis); 3,520,179

(Reed); 3,604,247 (Gramain et al.); 3,666,999 (Moreland, Jr. et al.); 3,680,362 (Geerdes et al.); 3,699,804 (Gassmann et al.); 3,713,328 (Aritomi); 3,782,173 (Van Vessem et al.) 3,864,962 (Stark et al.); 3,908,441 (Virloget); 3,952,577 (Hayes et al.); 3,990,295 (Renovanz et al.); 4,149,405 (Ringrose); 4,302,965 (Johnson et al.); 4,426,878 (Price et al.); 4,432,761 (Dawe); 4,616,503 (Plungis et al.); 4,637,250 (Irvine, Jr. et al.); 4,680,957 (Dodd); 4,680,958 (Ruelle et al.); 4,750,351 (Ball); 4,856,322 (Langrick et al.); 4,899,575 (Chu et al.); 5,142,899 (Park et al.); 5,222,497 (Ono); 5,224,375 (You et al.); 5,257,529 (Taniguchi et al.); 5,327,778 (Park); and 5,365,776 (Lehmann et al.).

A device called the "Hevimet 40" has recently been advertised at www.hevimet.freeserve.co.uk. The Hevimet 40 device is stated to be a whole blood and plasma viscometer that tracks the meniscus of a blood sample that falls due to gravity through a capillary. While the Hevimet 40 device may be generally suitable for some whole blood or blood plasma viscosity determinations, it appears to exhibit several significant drawbacks. For example, among other things, the Hevimet 40 device appears to require the use of anti-coagulants. Moreover, this device relies on the assumption that the circulatory characteristics of the blood sample are for a period of 3 hours the same as that for the patient's circulating blood. That assumption may not be completely valid.

The following U.S. patents disclose viscosity or flow measuring devices, or liquid level detecting devices using optical monitoring: U.S. Pat. Nos. 3,908,441 (Virloget); 5,099,698 (Kath, et. al.); 5,333,497 (Br nd Dag A. et al.). The Virloget '441 patent discloses a device for use in viscometer that detects the level of a liquid in a transparent tube using photodetection. The Kath '698 patent discloses an apparatus for optically scanning a rotameter flow gauge and determining the position of a float therein. The Br nd Dag A. '497 patent discloses a method and apparatus for continuous measurement of liquid flow velocity of two risers by a charge coupled device (CCD) sensor.

A statutory invention registration, H93 (Matta et al.) discloses an apparatus and method for measuring elongational viscosity of a test fluid using a movie or video camera to monitor a drop of the fluid under test.

Notwithstanding the existence of the foregoing technology, a need remains for an apparatus and method for obtaining the viscosity of both Newtonian fluids and non-Newtonian fluids (e.g., blood) over a range of shears, including low shear ranges (e.g., $0.1s^{-1}$), and where flow rate and pressure drop measurements can be avoided and where the viscosity determination can be conducted in a short span of time.

SUMMARY OF THE INVENTION

Accordingly, it is an object of the present invention to substantially obviate one or more of the problems associated with the related art.

It is an object of the present invention to provide an apparatus and method for obtaining the viscosity of both Newtonian fluids and non-Newtonian fluids over a range of shear rates in real time.

It is another object of the present invention to provide an apparatus and method for obtaining the viscosity of non-Newtonian fluids (e.g., circulating blood of a living being) over a range of shears, including low shear rates (e.g., $0.1s^{-1}$).

It is still another object of the present invention to provide an apparatus and method for obtaining the viscosity of both Newtonian fluids and non-Newtonian fluids where flow rate and pressure drop measurements can be avoided.

It is still another object of the present invention to provide an apparatus and method that detects the column heights of a plurality of fluid columns in a corresponding plurality of transparent containers substantially simultaneously while using a single detector.

These and other objects of the invention can be achieved by an apparatus for effecting the viscosity measurement of Newtonian and non-Newtonian fluids over a range of shear rates. The apparatus comprises: a pair of tubes having respective ends coupled to a source of Newtonian or non-Newtonian fluid and wherein each of the tubes comprises a respective capillary tube and wherein the capillary tubes have different lengths; a respective valve in each of the tubes for controlling the fluid flow from the fluid source; an analyzer, coupled to the valves, for controlling the valves to permit the flow of fluid into the pair of tubes whereupon the fluid in each of the pair of tubes assumes the same initial position with respect to a reference position. The analyzer is arranged for operating the valves so that the position of the fluid in each of the tubes changes away from the same initial position. The analyzer is also arranged for monitoring the fluid position change in each of the tubes and calculating the viscosity of the fluid based thereon.

These and other objects of the invention can also be achieved by an apparatus for monitoring the level of a plurality of columns of fluid in a respective plurality of transparent containers substantially simultaneously. The apparatus comprises: an optical source of light for each one of the plurality of columns of fluid and wherein each of the optical sources emits a respective light ray at its corresponding transparent container; and a single detector for detecting at least a portion of each respective light ray that impinges on the corresponding transparent container substantially simultaneously.

These and other objects of the invention can also be achieved by a method for effecting the viscosity measurement of Newtonian and non-Newtonian fluids over a range of shear rates, said method comprising the steps of: (a) providing a pair of tubes each having an end coupled to a source of Newtonian or non-Newtonian fluid and each tube comprising respective capillary tube portions and wherein each of the respective capillary tube portions have lengths different from each other and wherein each of the tubes comprise a valve; (b) activating the respective valves to generate a respective fluid flow from the source through each of the pair of tubes; (c) de-activating the respective valves to establish a same initial position of fluid in each of the tubes with respect to a reference position; (d) re-activating the respective valves so that the position of fluid in each of the tubes changes away from the same initial position; (e) monitoring the fluid position change in each of said tubes; and (f) calculating the viscosity of the fluid based thereon.

These and other objects of the invention can also be achieved by a method for monitoring the level of a plurality of columns of fluid in a respective plurality of transparent containers. The method comprises the steps of: (a) directing a respective ray of light at its corresponding transparent container; and (b) detecting at least a portion of each of the respective light rays that impinges upon the transparent container and wherein the at least a portion of each of the respective light rays that are detected comprises that portion of the light rays that does not encounter any fluid in the transparent containers.

DESCRIPTION OF THE DRAWINGS

Other objects and many of the intended advantages of this invention will be readily appreciated when the same becomes better understood by reference to the following detailed description when considered in connection with the accompanying drawings wherein:

FIG. 8 depicts a graphical representation of the respective columns of fluid in the riser tubes of the DRDC viscometer versus time during the viscosity test run;

FIG. 11A depicts a graphical representation of the viscosity of a non-Newtonian test fluid, e.g., a living being's circulating blood, plotted for a range of shear rates obtained from the present invention; and FIG. 11B depicts a graphical representation of the logarithm of the viscosity of a non-Newtonian test fluid, e.g., a living being's circulating blood, plotted against the logarithm of shear rates obtained from the present invention.

DETAILED DESCRIPTION OF THE PREFERRED EMBODIMENTS

The present invention discloses an apparatus and method for determining the viscosity of Newtonian fluids (e.g., water, plasma, etc.) as well as non-Newtonian fluids (blood). The apparatus and method of the present invention can be coupled to a static source (e.g., a sample or specimen) or a dynamic source (e.g., the circulating blood of a living being) of either of these types of fluids. In particular, where the viscosity of the circulating blood or plasma (or other biological fluid of a living being) is desired, the fluid source is the circulating fluid of the living being (e.g., a vein, if blood/plasma viscosity is to be determined), as shown in U.S. Pat. No. 6,019,735 entitled VISCOSITY MEASURING APPARATUS AND METHOD OF USE and in Co-Pending application Ser. No. 09/439,795, filed Nov. 12, 1999, now U.S. Pat. No. 6,322,524, entitled DUAL RISER/SINGLE CAPILLARY VISCOMETER, both of which are incorporated by reference herein. On the other hand, where the viscosity of artificial fluids, such as paints, polish, etc., are to be determined, a static sample or specimen can serve as the fluid source. Thus, it should be understood that the apparatus and method of the present invention are not limited by either the type of fluid (i.e., Newtonian or non-Newtonian) nor the fluid source (static or dynamic).

The following discussion of the apparatus and method of the present invention uses the circulating blood of a living being as the fluid source. It should be understood that this is by way of example only and not by way of limitation.

For measuring the viscosity of circulating blood, including whole blood, of a living being, the apparatus and method as disclosed in U.S. Pat. No. 6,019,735 are generally preferable. To negate venous pressure effects at low shear rates, cuffing the living being, or other suitable means, may be used with that apparatus and method.

Figure 1:
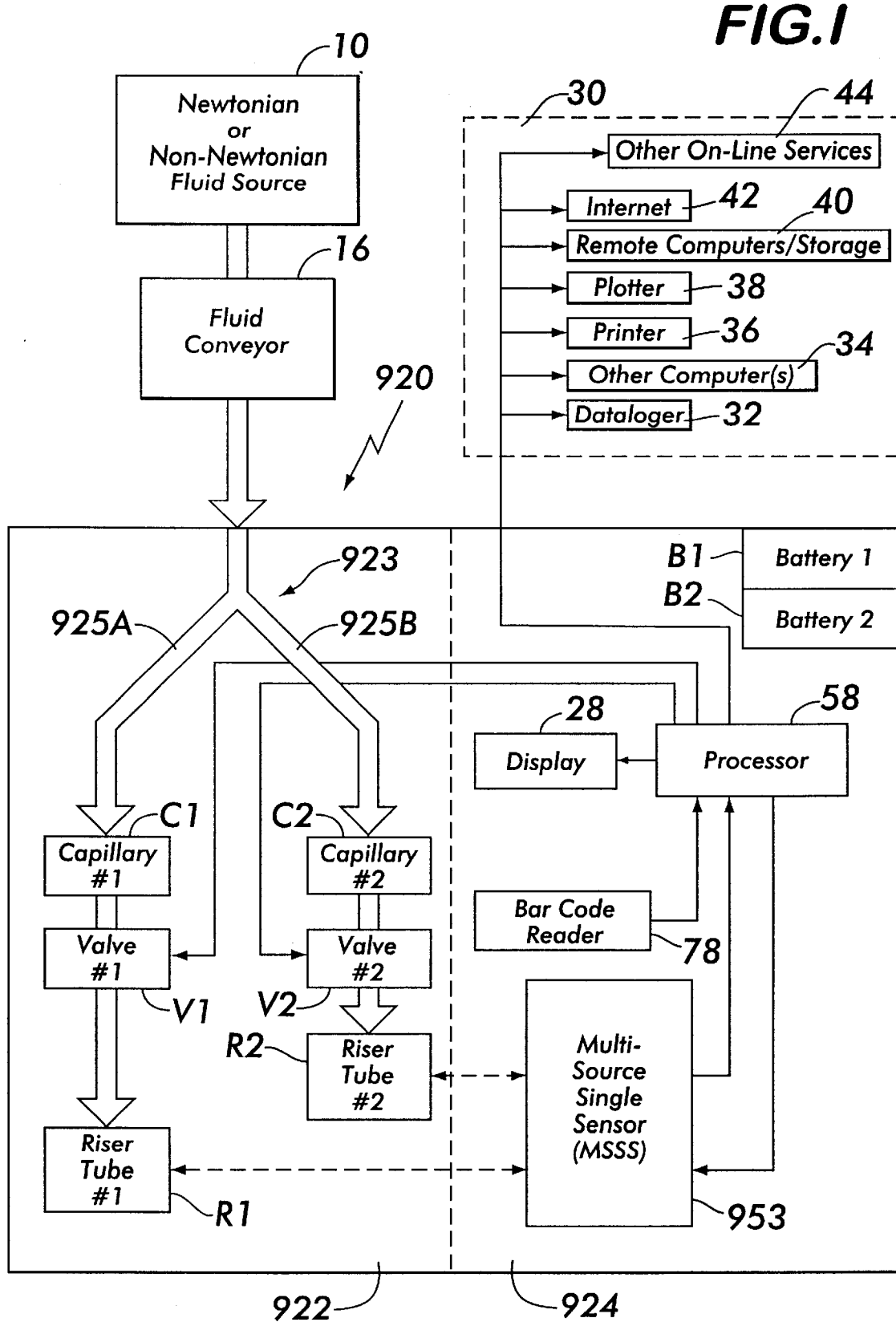
FIG. 1 is a block diagram of the dual capillary/dual riser (DRDC) viscometer.

An alternative apparatus and method of the present invention to negate pressure at low shear rates for measuring the viscosity of circulating blood, including whole blood, of a living being is shown generally at 920 in FIG. 1. The dual riser/dual capillary (DRDC) viscometer 920 basically comprises a fluid receptor 922 and an analyzer/output portion 924. The fluid source 10 is coupled to the DRDC viscometer 920 through a fluid conveyor 16 (e.g., where the viscosity of a biological fluid such as blood is to be determined, the fluid conveyor 16 may comprise a needle, an IV needle, an in-dwelling catheter, etc., or any equivalent structure that can convey circulating blood from a patient 10 to the DRDC viscometer 920). As will be discussed in detail later, the analyzer/output portion 924 provides a display 28 for presenting the viscosity information, as well as other information to the operator. The analyzer/output portion 924 may also provide this information to other suitable output means 30, such as a datalogger 32, other computer(s) 34, a printer 36, a plotter 38, remote computers/storage 40, to the Internet 42 or to other on-line services 44.

The fluid receptor 922 basically comprises a Y-branch 923 for dividing the input fluid flow into two paths 925A/925B comprising respective capillaries, C1 and C2, of known dimensions. In the preferred embodiment, the diameters of the capillaries C1/C2 are similar (e.g., 0.8 mm inside diameter) but each comprises different lengths; it should be understood that the diameters of the capillaries C1 and C2 could also be different. The diameters of the capillary tubes C1 and C2 are selected to ensure that the friction losses in the tubes are dominant losses in the paths 925A/925B. The output of the capillaries C1 and C2 are coupled to respective valves, V1 and V2. The output of the valves V1/V2 are coupled to the input of respective riser tubes R1 and R2. Each of the riser tubes R1 and R2 are preferably the same dimensions (e.g., 12 inch long, 2 mm inside diameter). As will be discussed in detail later, the valves V1 and V2 allow for control of the respective flow paths 925A/925B prior to the viscosity test run. The upper ends of the riser tubes R1 and R2 are open to ambient air.

Figure 2:
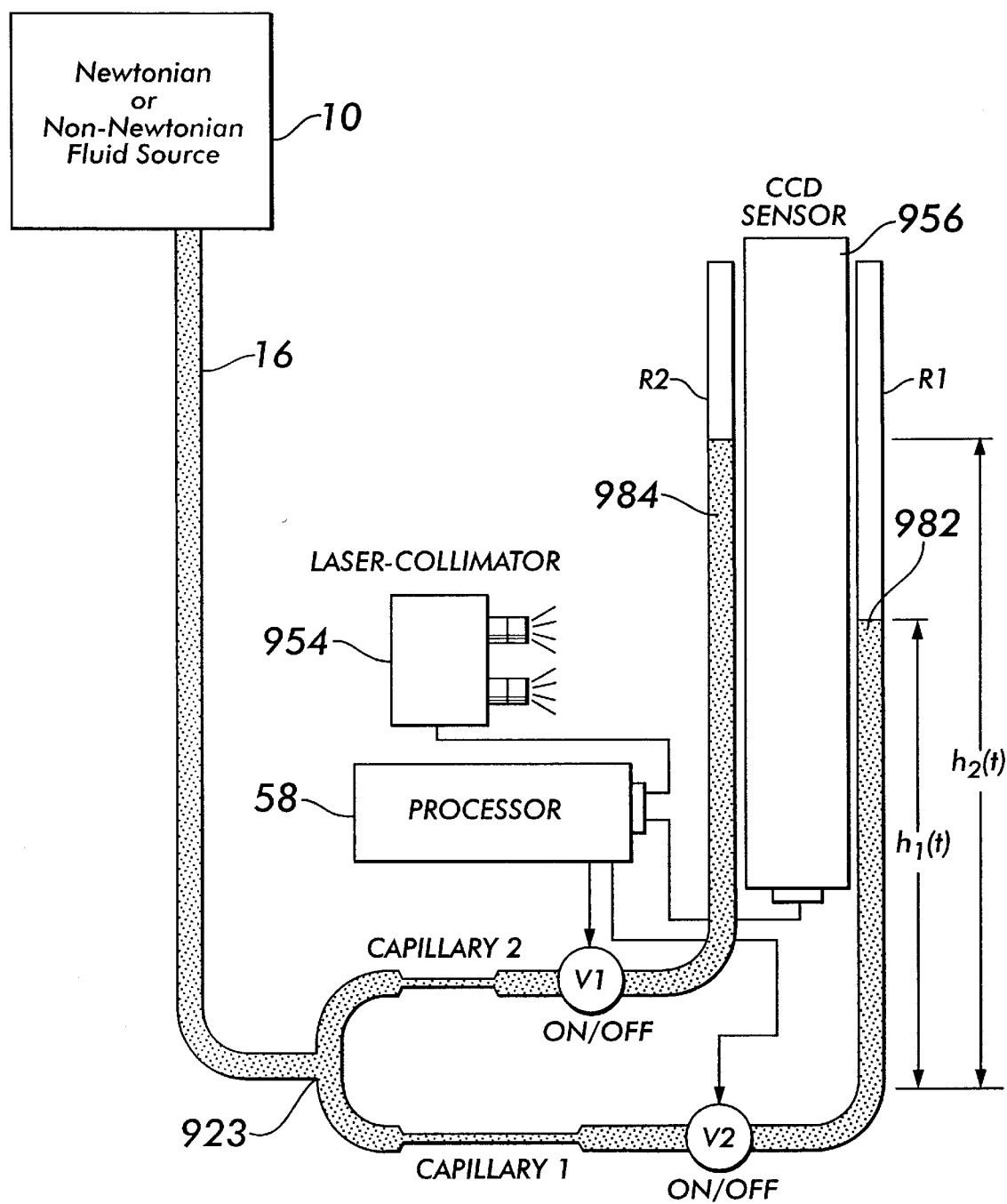
FIG. 2 is a functional diagram of the DRDC viscometer during the viscosity test run.

The analyzer/output portion 924 basically comprises a multi-source single sensor (MSSS) 953, a processor 58, the display 28, a bar code reader 78, and a first battery B1 and a second back-up battery B2. The MSSS 953 basically comprises an interrogation portion 954 (e.g., a laser/collimator, as will be discussed later) and a detection portion 956 (e.g., a CCD sensor), as shown most clearly in FIG. 2; the MSSS 953 monitors the respective fluid column levels 982 and 984 in the riser tubes R1/R2 that is used for generating the height vs. time data, as will also be described later. All of this data is passed to the processor 58.

The processor 58 (e.g., a "386" microprocessor or greater, or any equivalent) is arranged to analyze the data from the MSSS 953 and calculate the fluid viscosity therefrom, as will also be discussed in detail later. Furthermore, the processor 58 also controls the display 28 for providing the viscosity information and the other information to the operator as well as to the other output means 30. The processor 58 also controls the valves V1/V2 based on the data from the MSSS 953, as will be discussed later. Battery B1 provides all of the requisite power to the analyzer/output portion 924, with battery B2 serving as a back-up power supply. The bar code reader 78 will be described later.

Figure 3:
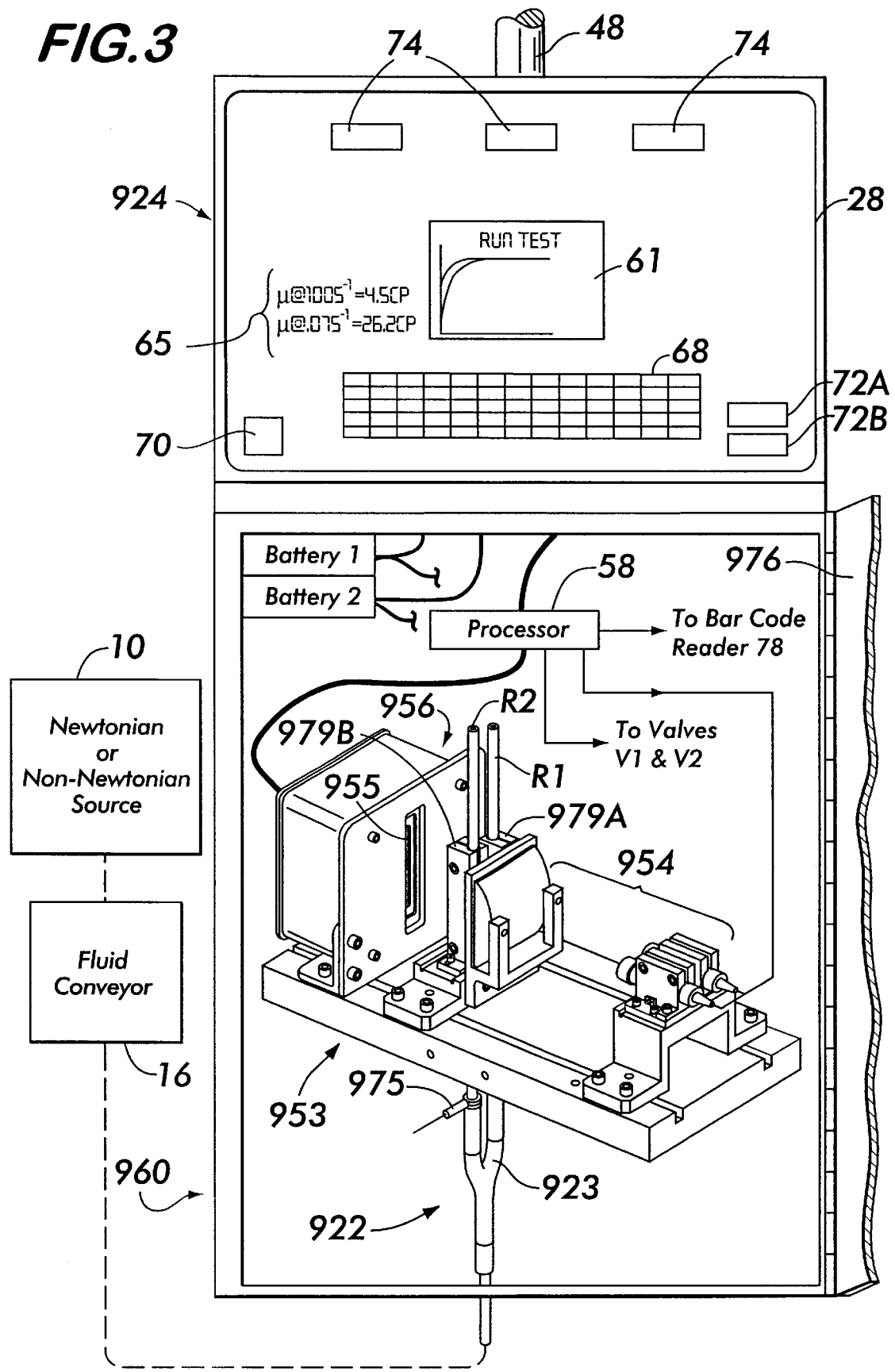
FIG. 3 is a front view of the DRDC viscometer showing the main body housing containing the fluid receptor positioned in the multi-source single sensor (MSSS), and the analyzer/output portion.
Figure 4:
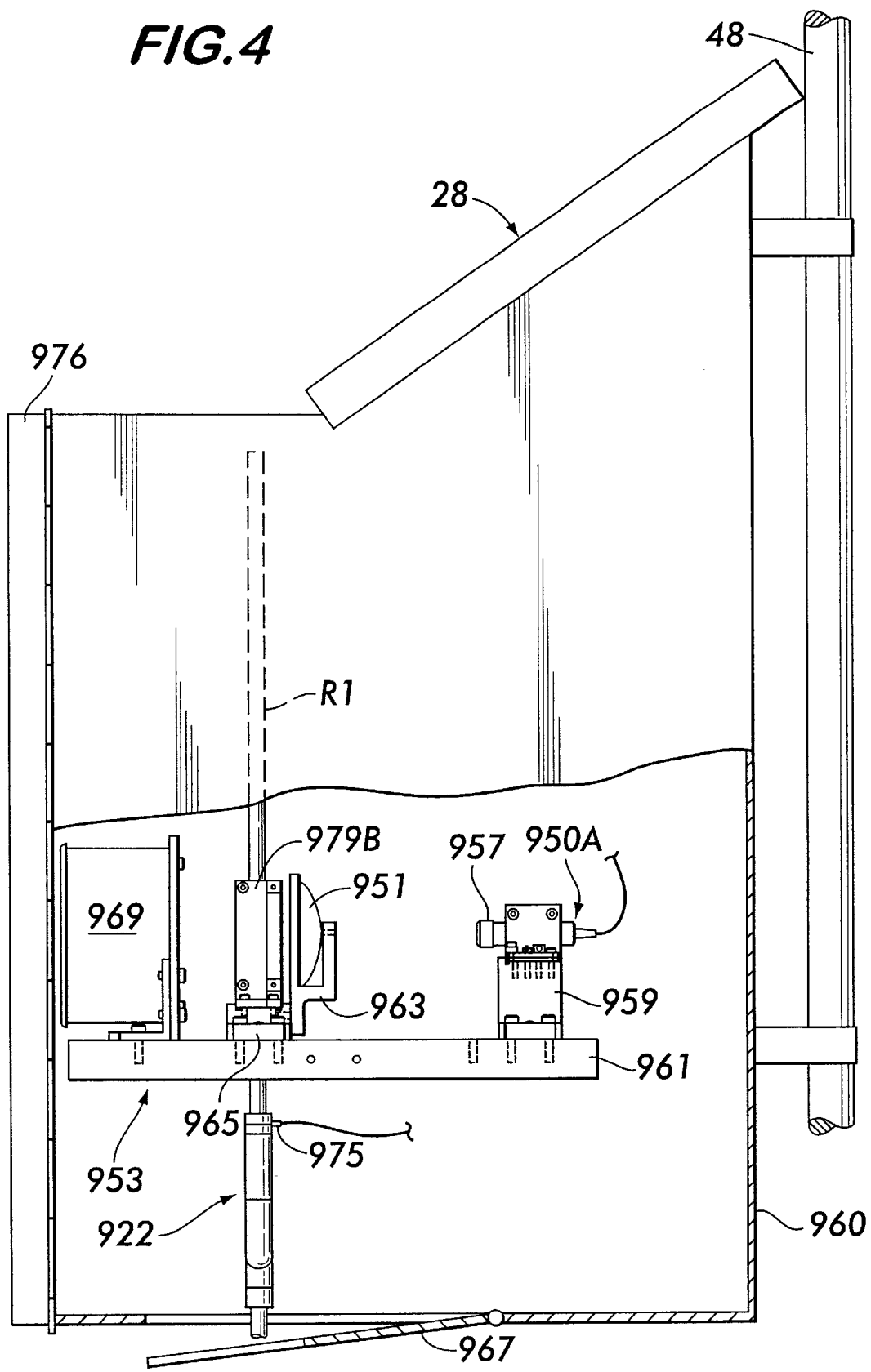
FIG. 4 is a partial cut-away side view of the DRDC viscometer of FIG. 3, showing the fluid receptor positioned in the MSSS.
Figure 4A:
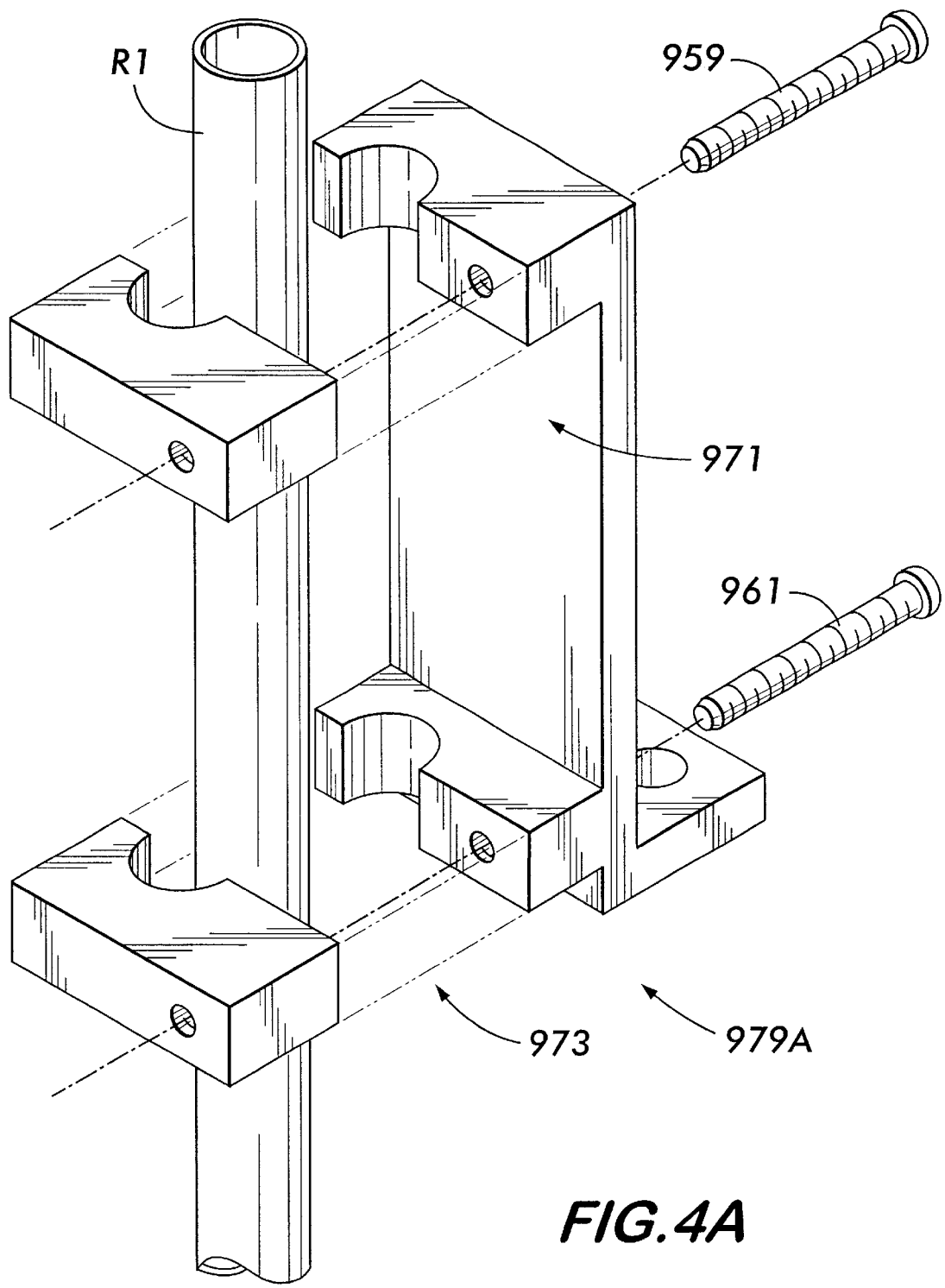
FIG. 4A is an exploded isometric view of one of the clamps of the MSSS that holds a riser tube.

As shown more clearly in FIGS. 3–4, the preferred embodiment of the DRDC viscometer 920 comprises the display 28 located above a main body housing 960. As shown most clearly in FIG. 4, the housing 960 is releasably secured to a frame, e.g., a conventional intravenous (IV) pole 48, while the display 28 is positioned in an inclined orientation; this facilitates user operation and viewing of the display 28. Except for the display 28, the fluid receptor 922 and the analyzer/output portion 924 are located within the housing 960. A door 976 is provided to the housing 960 for gaining access to the fluid receptor 922 and analyzer/output portion 924. Where the fluid receptor 922 is a disposable assembly, (e.g., where biological fluids such as blood or plasma are being tested), a release hatch 967 (FIG. 4) in the bottom of the housing 960 permits the fluid receptor 922 to be replaced. In particular, the Y-branch 923, capillaries C1/C2, valves V1/V2 and riser tubes R1/R2 are disposable as an assembly. Moreover, as shown in FIGS. 3–4, the fluid receptor assembly 922 is releasably secured between the interrogation portion 954 of the MSSS 953 and the detection portion 956 of the MSSS 953. A pair of clamps 955A/955B releasably secure riser tubes R1 and R2 respectively in front of a collimator 951 (to be discussed later) and the interrogation portion 956 of the MSSS 953. FIG. 4A depicts one of these clamps, namely clamp 979A, it being understood that a similar clamp structure forms the clamp 979B. By loosening a pair of screws 959 and 961, an upper clamp portion 971 and a lower clamp portion 973, the riser tube R1 is released from the MSSS 953; and by disconnecting a quick-disconnect electrical connector 975 (only one of which is shown in FIG. 3) for valves V1 and V2, the fluid receptor assembly 922 can be drawn downward and out of the open release hatch 967. A new fluid receptor assembly 922 is then inserted into the MSSS 953 and the clamping process and is reversed and the electrical connectors 975 coupled to the respective valves. The DRDC viscometer 920 is then ready for a new viscosity test run.

On the other hand, where the fluid receptor 922 is non-disposable, the components (the Y-branch 923, capillaries C1/C2, valves V1/V2 and riser tubes R1/R2 ) can be thoroughly washed and cleaned in place in preparation for the next viscosity test run.

It should be understood that the above housing configuration is exemplary only and that other designs can be utilized without limiting the scope of the invention.

The display 28 (FIG. 3) of the analyzer/output portion 924 may comprise any suitable conventional devices, e.g., an ELD (electroluminescent display) or LCD (liquid crystal display) that permits the visualization of both text and graphics. The resolution of this display 28 is preferably 800×600 VGA or above. Furthermore, while the preferred embodiment utilizes a touch screen display which incorporates, among other things:
graphical display 61
instruction, and/or data, display 65 (which also includes the command line display shown as "RUN TEST"; e.g., "TESTING", "TEST IN PROGRESS," etc.)
alphanumeric keypad 68
emergency stop button 70
battery status indicators, 72A and 72B
function buttons 74,
it should be understood that any equivalent display device is within the broadest scope of the invention. Thus, any number of user interfaces and buttons may be available through the display 28. Therefore the invention 920 is not limited to the embodiment that is shown in FIG. 3. Moreover, the display 28 can be operated to minimize or maximize, or overlay any particular graphic or text screen, as is available in any conventional object-oriented operating system, such as Microsoft® WINDOWS.

As mentioned earlier, the MSSS 953 comprises an interrogation portion 954 and a detection portion 956 for simultaneously monitoring the movement of the columns 982 and 984 in the riser tubes R1 and R2. The interrogation portion 954 comprises a pair of lasers 950A/950B, a single collimating lens 951 and a single detector 955, e.g., a CCD array (FIG. 3) inside the detection portion 956, hence the phrase "multi-source, single sensor, since the sensor uses a single CCD sensor to collect data (multiple measurements) from multiple sources.

Figure 5:
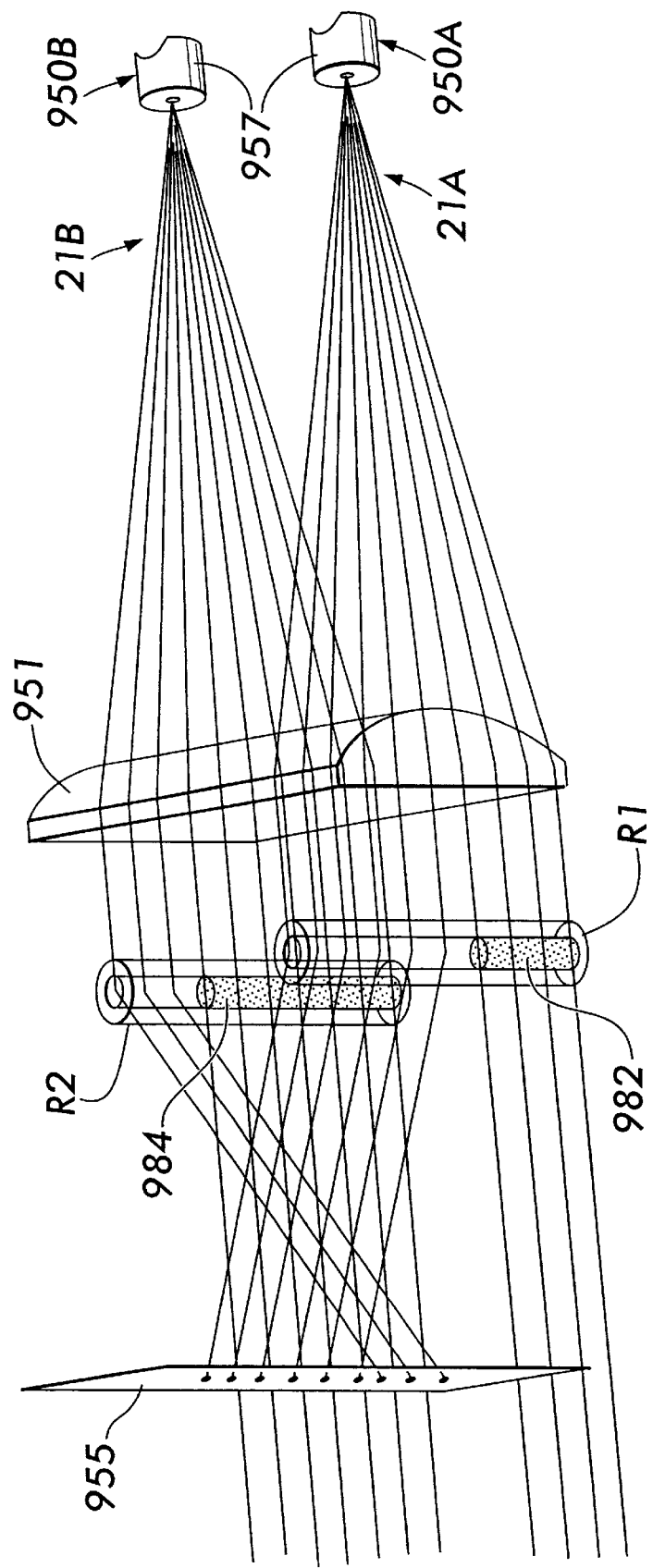
FIG. 5 is a functional diagram of how the MSSS detects the column heights of the two riser tubes.

FIG. 5 depicts the operation of the MSSS 953. Each laser 950A and 950B emits a respective light beam 21A and 21B that is focused by a sheet collimator 951 toward a respective riser tube R1 and R2. If there is air in a respective riser tube, before emerging from the other side of the riser tube, the corresponding light beam is refracted four different times. The light angles are calculated such that the light beams hit the CCD array 955 when there is air in the riser tube. On the other hand, if the light encounters the fluid columns 982 or 984, in the riser tube R1 and R2, respectively, wherein the fluid has an index of refraction different from air, $n_a$, the light beam is refracted away from the CCD array 955 and the light beam never hits the pixels of the CCD array 955. The measurement is taken from one laser at a time, alternating at a speed almost equal to the refresh rate of the CCD array 955 pixels; in this manner, riser tube column heights of differing levels can be measured simultaneously. In fact, using this method, up to six riser tubes can be measured at a time. In particular, the lasers 950A/950B and sheet collimator 951 form a "sheet" collimated, monochromatic source which illuminates each riser tube. (This "sheet" can be described as a plane of light in which none of the rays which makes up the plane converge or diverge.) The riser tube, in general, has a well-defined geometry (in this case, cylindrical shell) that refracts the incoming light and deflects it towards the single detector 955 (the riser tube acts as a hollow cylindrical lens with a well-defined focal length) focal point. If the line of impingement on the riser tube is well known, the CCD sensor can be placed such that the refracted light will illuminate its surface resulting in a strong signal. If a portion of the light path is blocked with an opaque fluid, there is a 1:1 correspondence of dark or non-illuminated pixels on the CCD sensor. In addition, if the fluid in the column has an index of refraction which greatly differs from the fluid with which the CCD sensor placement is calibrated (e.g., air is used as the calibrating fluid), the deflection of the impinging light is significantly altered and does not illuminate the relatively thin width of the CCD sensor 955.

FIGS. 3–4 depict an implementation of the MSSS 953 but it should be understood that the following components of this implementation are by way of example only and not by way of limitation.

Lasers 950A and 950B are 3.5 mW/5VDC TTL5-3.5G-670 laser diode modules manufactured by World Star Technologies of Ontario, Canada; furthermore, a line optics lens 957(LO-45, 16 mm ID×10 mm in length, also manufactured by World Star Technologies) is coupled to each 3.5 mW/5VDC TTL5-3.5G-670 laser diode module for proper laser diode output. The lasers 950A/950B are secured in a mounting bracket 959 that is in a sliding adjustable relationship with a base 961. The lasers 950A/950B are aimed at the sheet collimator 951 which is secured in its own mounting bracket 963. The sheet collimator 951 is a cylinder lens (PCX, H50157, 65 mm width×440 mm length; the 440 mm length is cut down to approximately 70 mm) manufactured by Edmund Scientific Co. The sheet collimator 951/bracket 963 is secured to another mounting bracket 965 that is also in a sliding adjustable relationship with the base 961. As mentioned earlier, the riser tubes R1/R2 are positioned inside riser tube clamps 979A and 979B.

The CCD array 955 is implemented using a Dalsa CL-C8-6000 A Turbosensor Camera which utilizes a Dalsa IL-C8-6000 sensor (pitch: 10 mm×10 mm; aperture 6.0 cm×10 mm; maximum camera line rate 4.9 kHz; output format is 8-bit digital 2 channel). The CL-C8-6000 A is a high-speed line scan camera that can provide high speed digitized video signals. The CL-C8-6000 A utilizes conventional CCD acquisition software. The CCD array 955 is positioned inside a housing 969 of the detection portion 956 which contains a window through which the collimated light beams enter.

The lasers 950A/950B alternate on/off with a 5V signal synchronized with the CCD array 955 so that the CCD array 955 always knows which laser's light beam is striking the array 955. In particular, the processor 58 comprises a software routine that controls the alternate activation of the lasers 950A/950B at high speed and in synchronization with the CCD array 955.

The door 976 (which can be vertically or horizontally hinged to the housing 260) is provided to establish a darkened environment during the test run. The door 976 also supports the bar code reader 78, mentioned earlier. This bar code reader 78 automatically reads a bar code (not shown) that is provided on one of the riser tubes (e.g., R2 ). The bar code contains all of the predetermined data regarding the characteristics of the capillary tubes C1/C2 (e.g., length and diameter) and the characteristics of the riser tubes R1 and R2. This information is passed to the processor 58 which is then used to determine the viscosity, as will be discussed in detail later. The bar code reader 78 passes this information to the processor 58. It should be understood that the location (on the door 976) of the bar code reader 78 is exemplary only and that other locations within the unit are encompassed by the scope of the invention.

The batteries B1/B2 may comprise a 12VDC, 4 amp-hour batteries, or any equivalent power supply (e.g., batteries used in conventional lap-top computers such as lithium ion batteries). The display 28 provides the status indicators 72A/72B for each battery in the DRDC viscometer 920. In particular, when the DRDC viscometer 920 is operating off of battery B1, the two battery indicators 72A/72B appear on the display 28. However, once battery B1 is depleted, the battery B1 indicator 72A disappears and the battery B2 indicator 72B blinks to warn the operator that the DRDC viscometer 920 is now operating off of the back-up battery B2 and re-charge of battery B1 is necessary.

Figure 6:
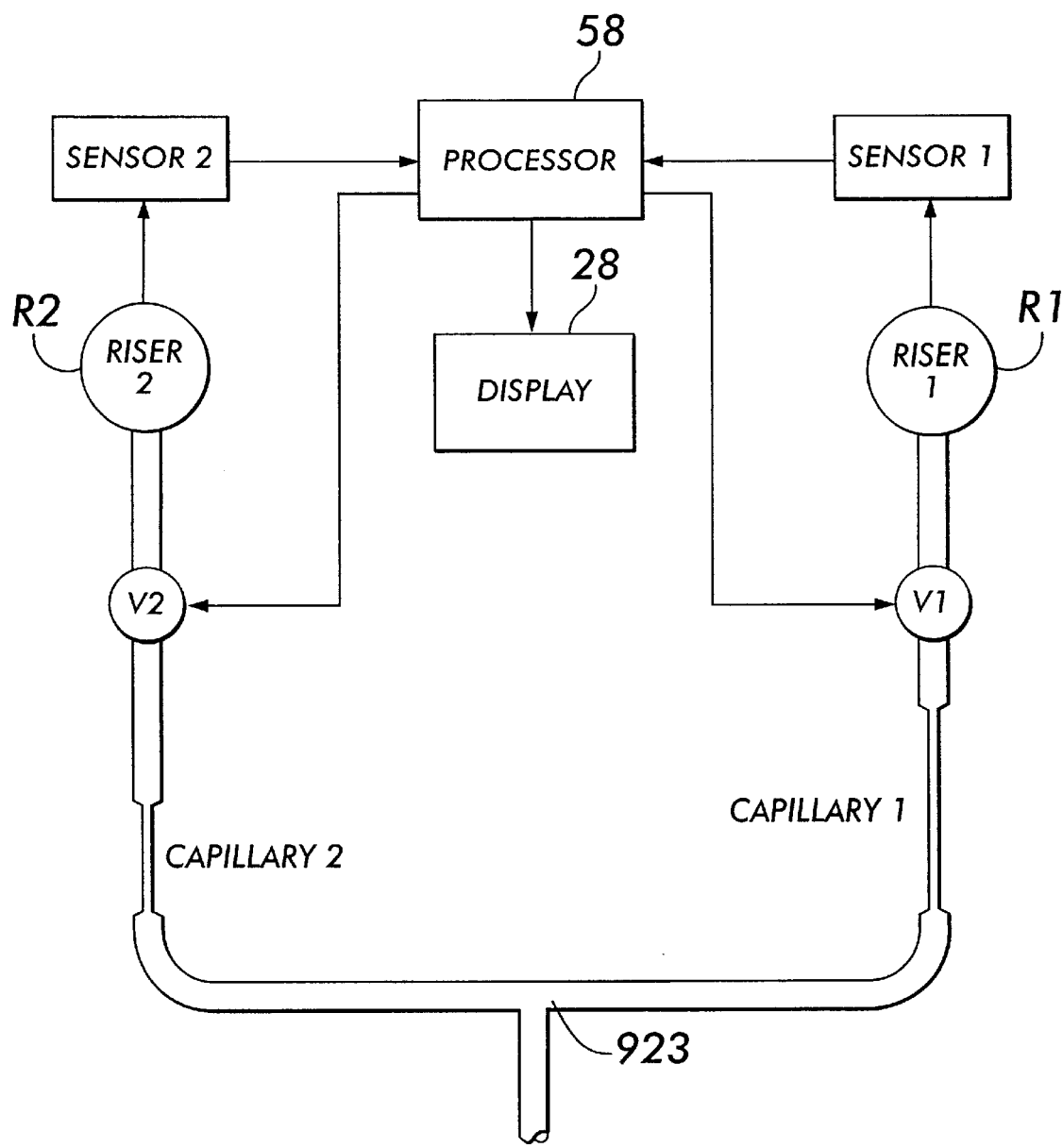
FIG. 6 is a block diagram for the DRDC viscometer which detects the movement of the column of fluid in each of the riser tubes using various types of sensors.

Alternatively, as shown in FIG. 6, it is within the broadest scope of the invention to include any means and/or method for detecting the movement of the columns of fluid 982/984 in the riser tubes R1 and R2 and, as such, is not limited to the MSSS 953 arrangement. In fact, the following type of physical detections (indicated by "SENSOR 1" and "SENSOR 2" in FIG. 6) are covered by the present invention:

d(Weight)/dt: the change in weight of each column of fluid with respect to time using a weight detecting means for each column of fluid as the sensor; e.g., $w_1(t)-w_2(t)$;

d(Pressure)/dt: the change in pressure of each column of fluid with respect to time using a pressure transducer located at the top of each column of fluid; e.g., $p_1(t)-p_2(t)$;

time of flight: the length of time it takes an acoustic signal to be emitted from a sensor (e.g., ultrasonic) located above each column of fluid and to be reflected and return to the sensor; e.g., time of $\text{flight}_1(t)$–time of $\text{flight}_2(t)$;

d(Volume)/dt: the change in volume of each column of fluid with respect to time; e.g., $V_1(t)-V_2(t)$;

d(Position)/dt: the change in position of each column level using a digital video camera; e.g., $Pos_1(t)-Pos_2(t)$;

d(Mass)/dt: the change in mass with respect to time for each column of fluid; e.g., $m_1(t)-m_2(t)$.

Operation of the DRDC viscometer 920 is discussed next.

Figure 7A:
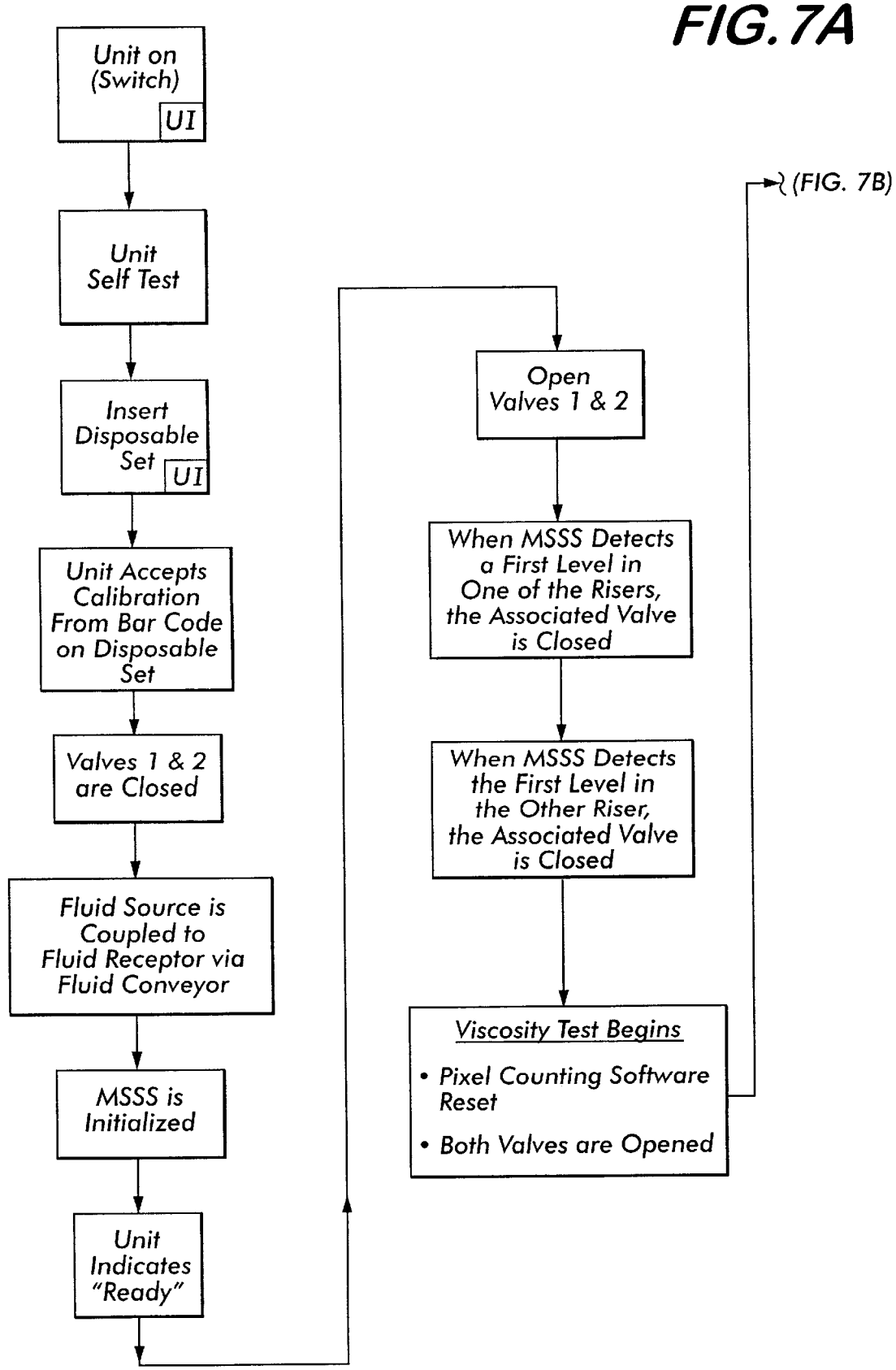
FIGS. 7A–7B together constitute a flow chart of the operation of the DRDC viscometer.
Figure 7B:
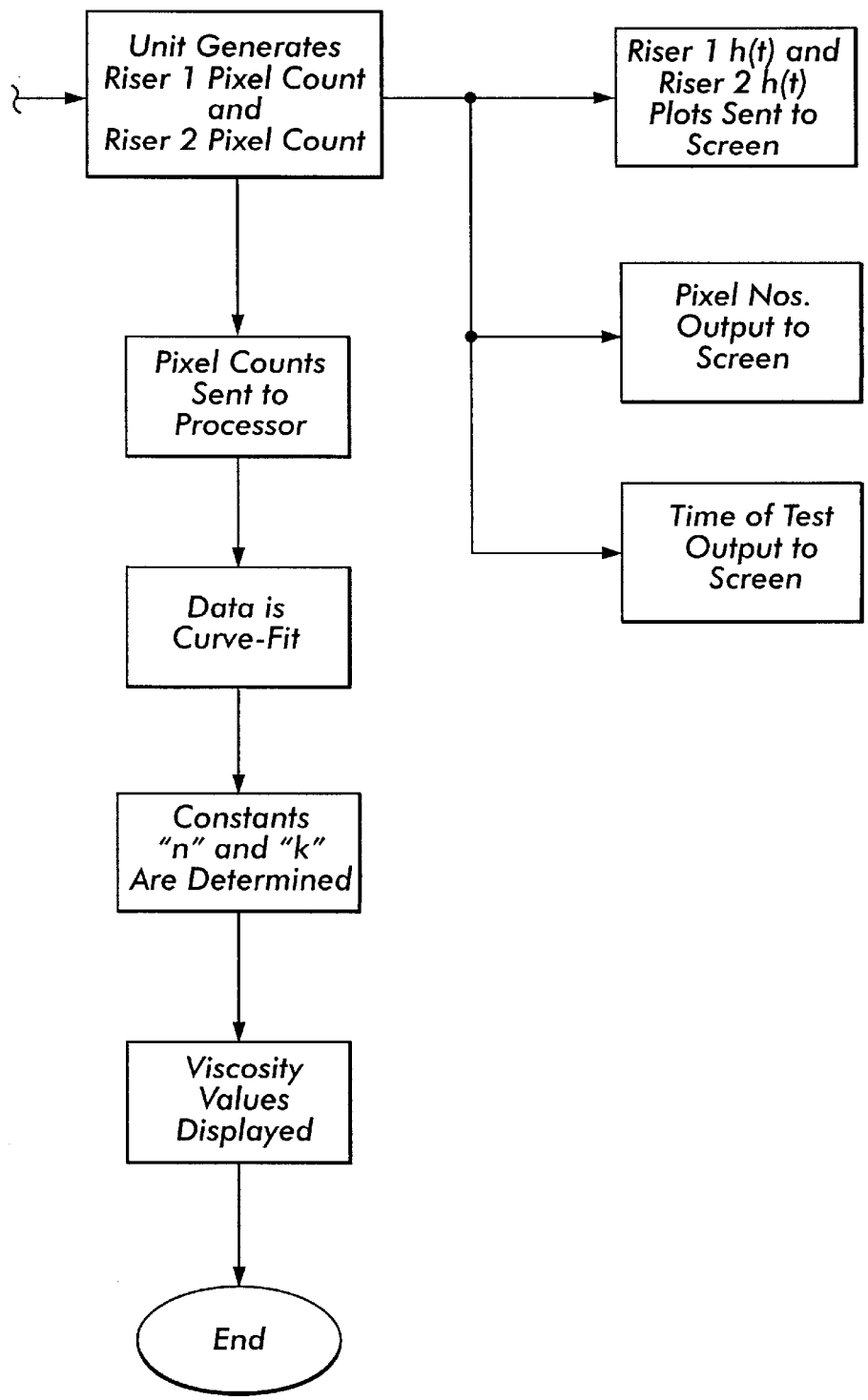

The flow chart of FIGS. 7A–7B depict the operation of the DRDC viscometer 920. The DRDC viscometer 920 is powered on whereby the DRDC 920 executes a self-test. If a disposable fluid receptor 922 is used, the assembly is installed, clamped and electrically connected to the valves V1/V2 at this time. The bar code reader 78 then obtains all the pertinent fluid receptor 922 information and provides that data to the processor 58. Next, the valves V1 and V2 are closed and then the fluid source 10, at an elevated position above the DRDC viscometer 920, is coupled to the DRDC 920 via the fluid conveyor 16. The MSSS 953 is initialized. The DRDC 920 then indicates it is ready to the operator. The valves V1 and V2 are then opened and the MSSS 953 begins monitoring both riser tubes R1 and R2. Because of the different lengths of the capillary tubes C1/C2, the time of appearance of the fluid columns 982 and 984 will differ. When the MSSS 953 detects a first level in one of the riser tubes R1 or R2, the associated valve V1 or V2 is closed and the MSSS 953 monitors the other riser tube until the other fluid column appears, at which time the other associated valve is closed. The pixel counting software in the MSSS 953 is then reset in order to prepare for the viscosity test run. Next, both valves V1 and V2 are opened and the MSSS 953 begins monitoring both columns 982/984 as they rise. The height vs. time characteristic of the two fluid columns is depicted in FIG. 8. During this viscosity test run, the R1 pixel count and the R2 pixel count data is generated and then sent to the processor 58 where the data is fitted to generate the plot shown in FIG. 8 which is displayed on the screen 28 as both a graphic representation as well as numerical data, along with the time of the test.

Figure 9A:
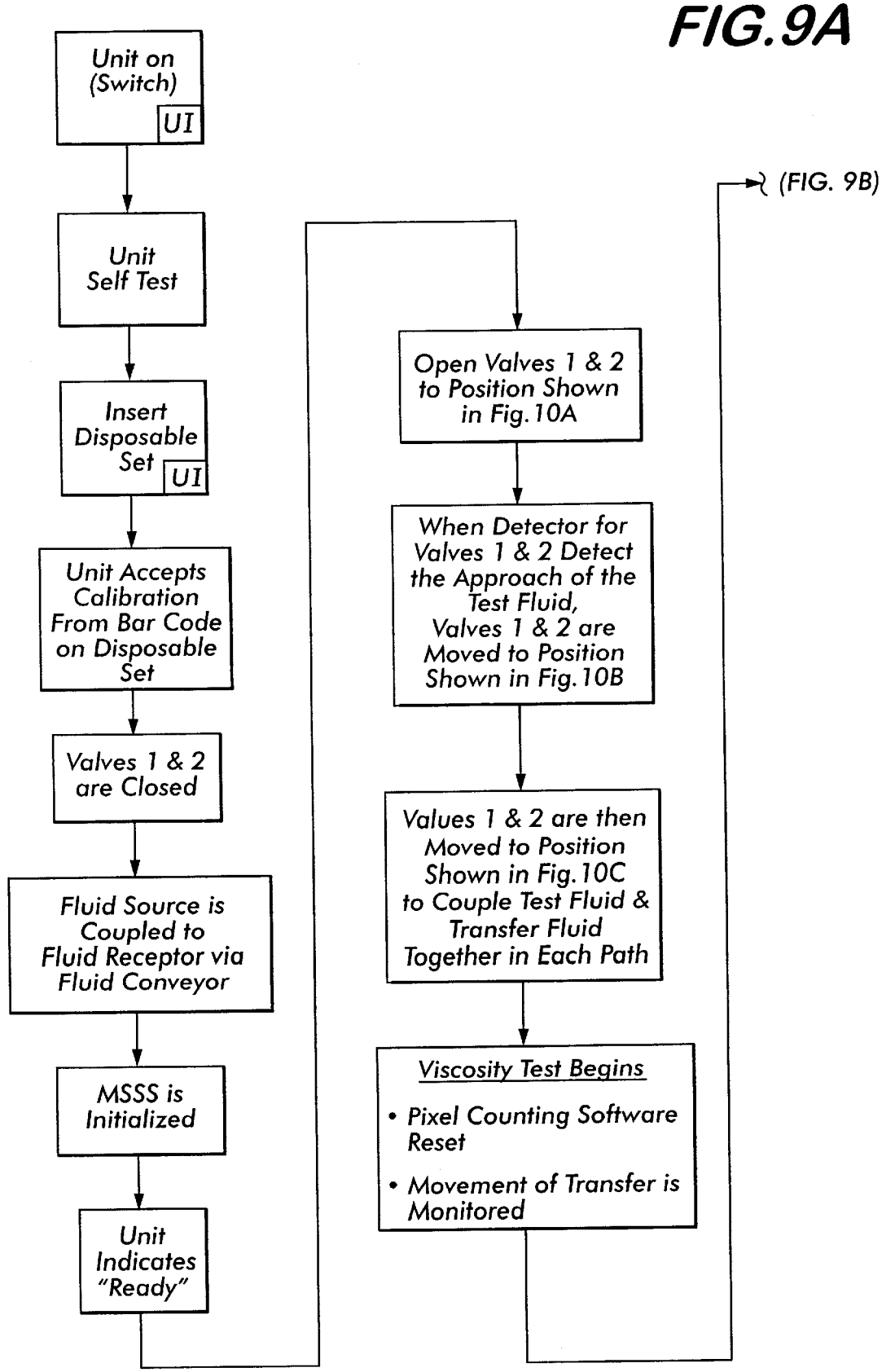
FIGS. 9A–9B together constitute a flow chart of the operation of the DRDC viscometer when a transfer fluid is used in each of the riser tubes.
Figure 9B:
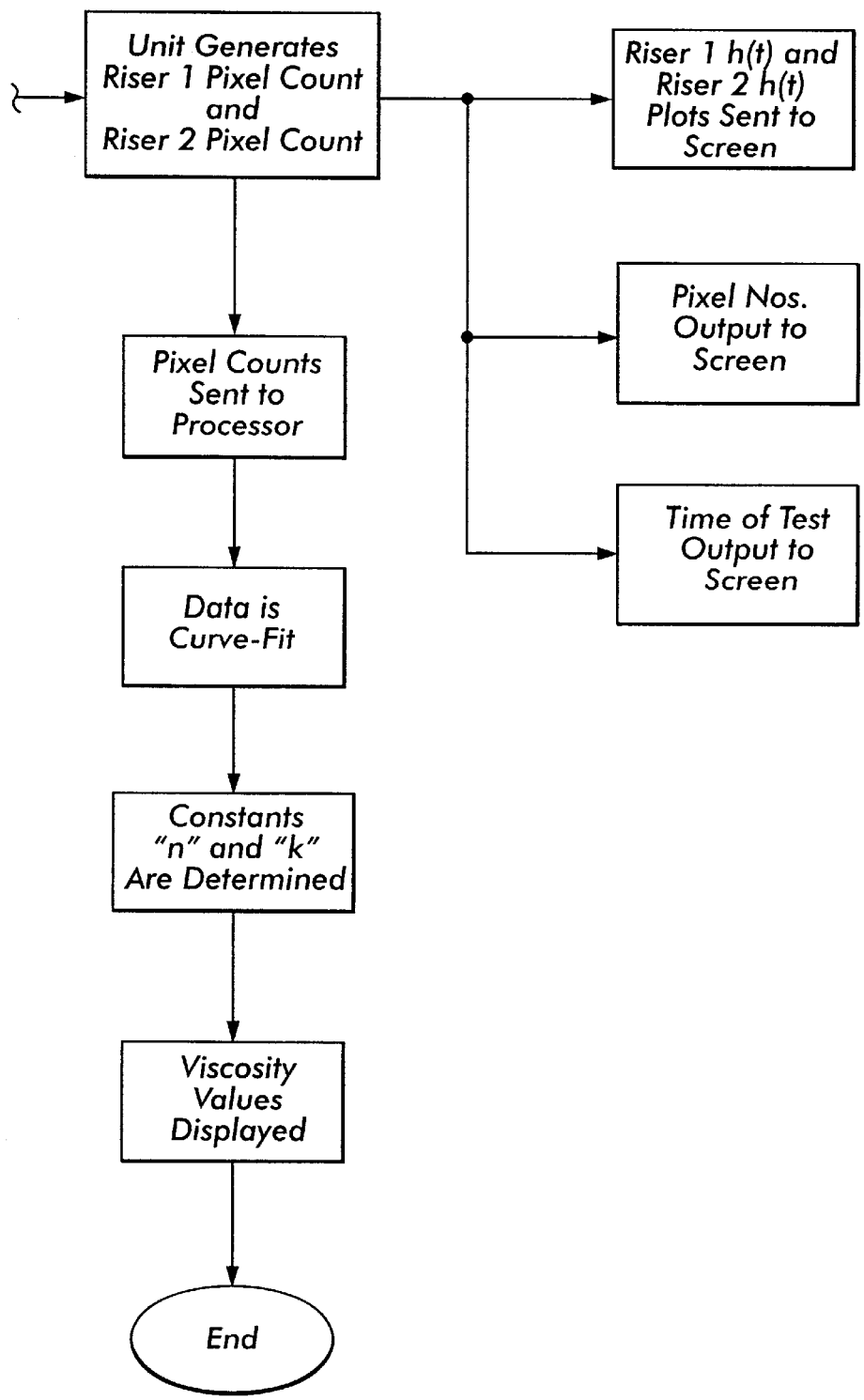
Figure 10A:
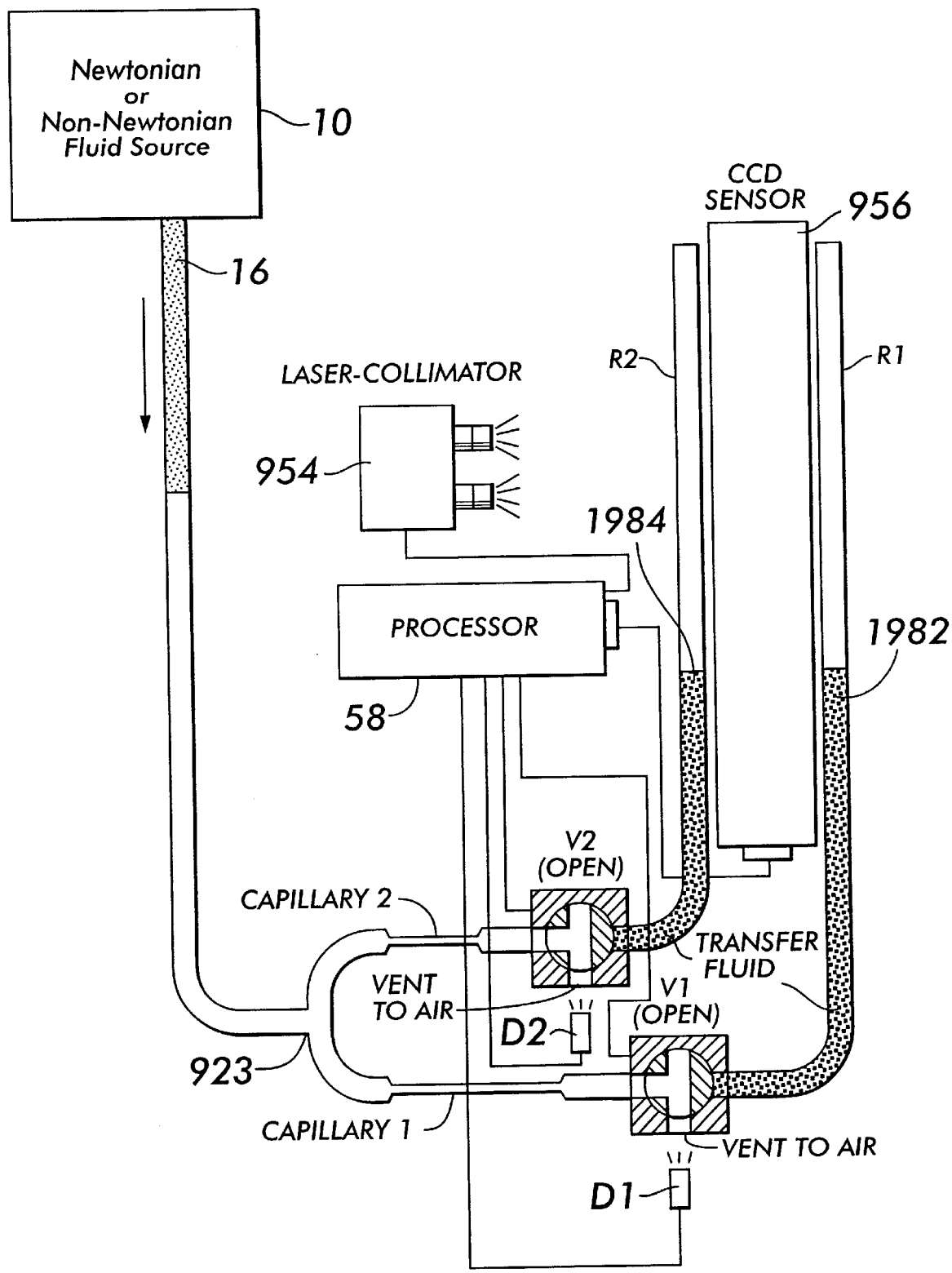
FIGS. 10A–10C comprise a functional view of the valve positions of the DRDC viscometer when a transfer fluid is used in the riser tubes.
Figure 10B:
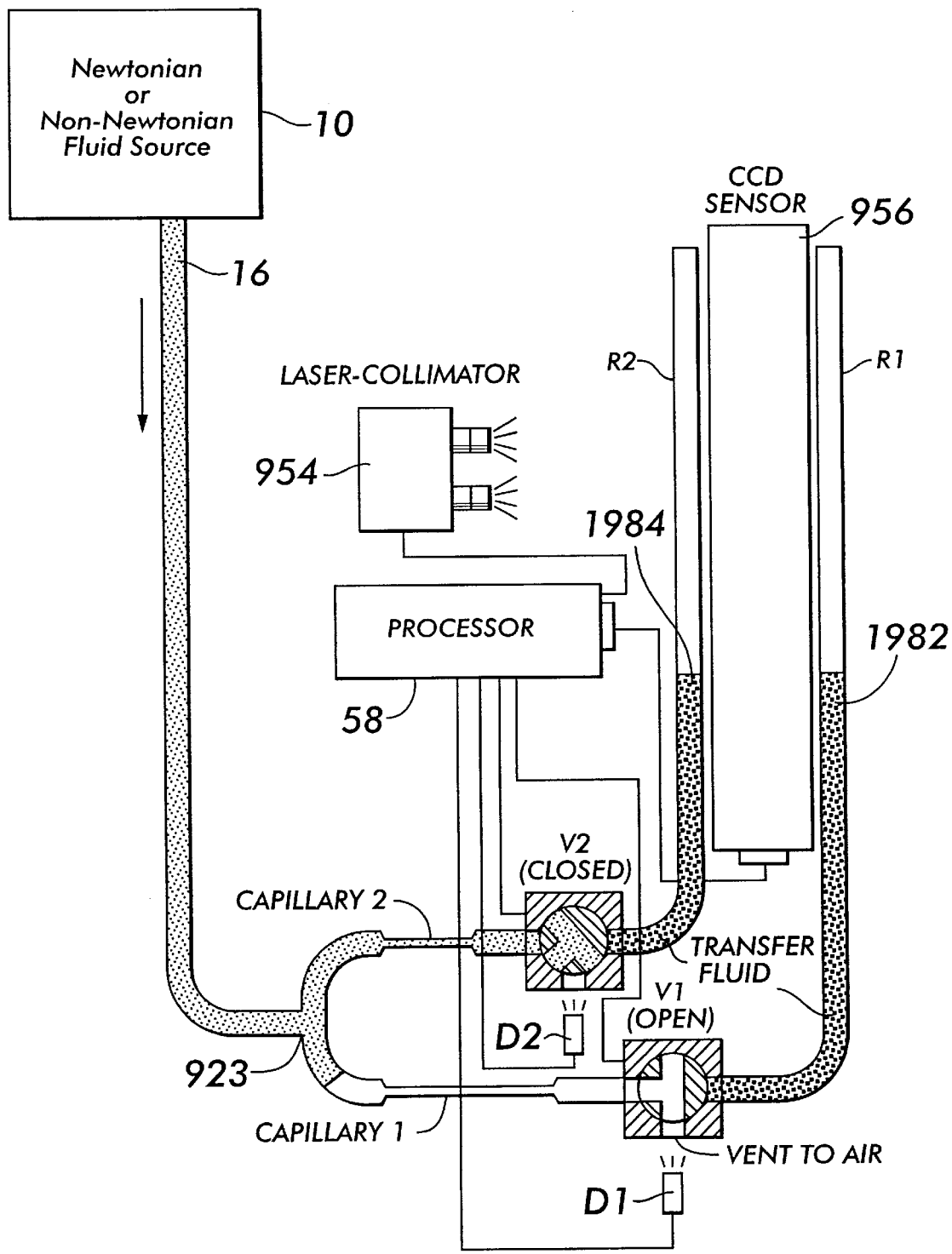
Figure 10C:
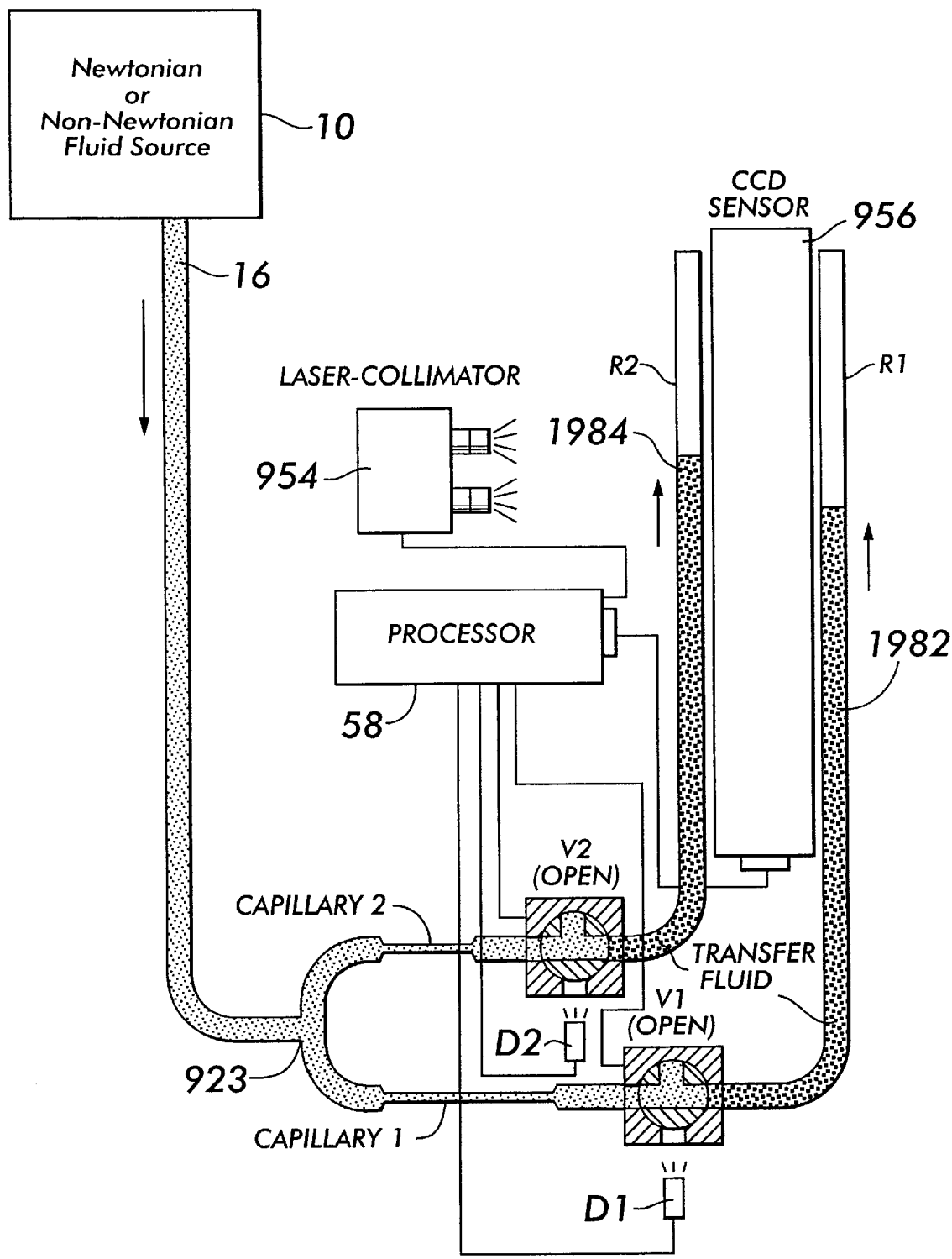

Alternatively, as described in application Ser. No. 08/919, 906 (now U.S. Pat. No. 6,019,735), the present invention 920 also can utilize an indicator or transfer fluid 29 (FIGS. 10A–10C, e.g., a liquid such as saline solution, alcohol, or any sterile water-type liquid) on the output of the valves V1 and V2 for "transferring" the motion of the test fluid from the fluid source 10; this is advantageous, for example, where the fluid source is a living being and the viscosity of the circulating blood of the living being is being determined. By using the transfer fluid 29, the amount of circulating blood actually leaving the living being to be monitored is minimized. Thus, the transfer fluid 29 is in fluid communication with the test fluid at its one end and forms the riser tube columns 1982 and 1984 at its other end. FIGS. 9A–9B depict the operation flowchart where a transfer fluid 29 is utilized. In order to properly couple the test fluid from the fluid source 10 to the transfer fluid 29, valves V1 and V2 are controlled, as set forth in the flowchart of FIGS. 9A–9B and as depicted in FIGS. 10A–10C. Detectors D1 and D2 (e.g., optical sensors, color detector, proximity sensors, etc.) monitor a respective valve to determine when the test fluid has entered the respective valve V1/V2, at which time the processor 58 is informed and the appropriate valve movement is taken in accordance with FIGS. 10A–10C.

It should be understood that alternatively, as shown in FIG. 6, it is within the broadest scope of the invention to include any means and/or method for detecting the movement of the columns of transfer fluid 1982/1984 in the riser tubes R1 and R2 and, as such, is not limited to the MSSS 953 arrangement. In fact, the following type of physical detections (indicated by "SENSOR 1" and "SENSOR 2" in FIG. 6) are covered by the present invention:

d(Weight)/dt: the change in weight of each column of transfer fluid with respect to time using a weight detecting means for each column of transfer fluid as the sensor; e.g., $w_1(t)-w_2(t)$;

d(Pressure)/dt: the change in pressure of each column of transfer fluid with respect to time using a pressure transducer located at the top of each column of transfer fluid; e.g., $p_1(t)-p_2(t)$;

time of flight: the length of time it takes an acoustic signal to be emitted from a sensor (e.g., ultrasonic) located above each column of transfer fluid and to be reflected and return to the sensor; e.g., time of $\text{flight}_1(t)-\text{time of flight}_2(t)$;

d(Volume)/dt: the change in volume of each column of transfer fluid with respect to time; e.g., $V_1(t)-V_2(t)$;

d(Position)/dt: the change in position of each transfer fluid column level using a digital video camera; e.g., $\text{Pos}_1(t)-\text{Pos}_2(t)$;

d(Mass)/dt: the change in mass with respect to time for each column of transfer fluid; e.g., $m_1(t)-m_2(t)$.

The determination of the test fluid viscosity is determined in accordance with the following:

The mathematical model of the flow physics begins with equations for the conservation of energy for each capillary tube between two points of interest in the system: 1) the capillary inlets and 2) the top of the fluid columns within the riser tubes. Assuming quasi-steady flow behavior, energy conservation equations, modified from Bernoulli's equations, can described both flow paths 925A/925B:

$$\left\{p_{VI} + \frac{1}{2}\rho V_{CI}^2 + \rho g h_{CI}\right\} - \left\{p_0 + \frac{1}{2}\rho V_{RI}^2 + \rho g h_1\right\} = \Delta p_{CI} + \Delta p_{SI} + p_{wI}$$

$$\left\{p_{V2} + \frac{1}{2}\rho V_{C2}^2 + \rho g h_{C2}\right\} - \left\{p_0 + \frac{1}{2}\rho V_{R2}^2 + \rho g h_2\right\} = \Delta p_{C2} + \Delta p_{S2} + p_{w2}$$

Where;

$\Delta p_{ci}$=capillary friction loss of tube i (i=1 or 2);

$\Delta p_{si}$=additional system friction losses in the flow path (e.g., fluid conveyor 16, Y-branch 923, riser tube R1/R2, etc.);

$p_{wi}$=wicking generated pressure at fluid/air interface (riser tube meniscus);

$p_{vi}$=static pressure at the capillary tube C1/C2 inlet;

$p_0$=static ambient pressure above the column of fluid 982/984 in the riser tubes R1/R2;

$\rho$=test fluid density (however, where a transfer fluid 29 is used, the density of the transfer fluid is used);

$V_{Ci}$, $V_{Ri}$=capillary and riser tube fluid velocities, respectively; and $h_{Ci}$, $h_r$=heights at capillary inlet and riser tube, respectively.

Additional assumptions are imposed to make the problem more tractable:

(1) $h_{C1,2}$ is selected as the reference height origin, (i.e. $h_{C1}=h_{C2}=0$).

(2) Additional system friction losses are assumed small in comparison with the capillary friction losses, (i.e., $\Delta p_{Si}<<\Delta p_{Ci}$). As mentioned earlier, the diameters of the capillary tubes C1 and C2 are selected to ensure that the friction losses in the tubes are dominant losses in the paths 925A/925B.

(3) The unknown capillary wicking forces for the two riser tubes R1/R2 are approximately equal, (i.e., $p_{w1} \approx p_{w2} \approx p_w$), thus, cancelling each other. This assumption is reasonable since the riser tubes are equal in diameter and surface properties.

The capillary and riser tube velocities may be written in terms of the measured quantities:

$$V_{Ri} = \frac{dh_i}{dt}$$

$$V_{Ci} = \left(\frac{\phi_R}{\phi_C}\right)^2 \frac{dh_i}{dt}$$

where, $\phi_R$, $\phi_C$=riser tube R1/R2 and capillary tube C1/C2 diameters, respectively.

Using the above assumptions, and substituting the velocity expressions into the energy conservation equation, results in the following.

$$p_{V1} - p_0 - \frac{1}{2}\rho\left\{\left(\frac{\phi_R}{\phi_C}\right)^4 - 1\right\}\left(\frac{dh_1}{dt}\right)^2 - \rho g h_1 - p_w = \Delta p_{C1}$$

$$p_{V2} - p_0 - \frac{1}{2}\rho\left\{\left(\frac{\phi_R}{\phi_C}\right)^4 - 1\right\}\left(\frac{dh_2}{dt}\right)^2 - \rho g h_2 - p_w = \Delta p_{C2}$$

Subtracting these questions;

$$p_{V1} - p_{V2} - \frac{1}{2}\rho\left\{\left(\frac{\phi_R}{\phi_C}\right)^4 - 1\right\}\left\{\left(\frac{dh_1}{dt}\right)^2 - \left(\frac{dh_2}{dt}\right)^2\right\} - \rho g(h_1 - h_2) =$$

$$\Delta p_{C1} - \Delta p_{C2}$$

Also, it may be shown from applying mass and momentum conservation at the Y-branch 923 that;

$$p_{V1} - p_{V2} = \frac{1}{2}\rho\left(\frac{\phi_R}{\phi_C}\right)^4\left\{\left(\frac{dh_2}{dt}\right)^2 - \left(\frac{dh_1}{dt}\right)^2\right\}$$

So that, $$\frac{1}{2}\rho\left\{2\left(\frac{\phi_R}{\phi_C}\right)^4 - 1\right\}\left\{\left(\frac{dh_2}{dt}\right) - \left(\frac{dh_1}{dt}\right)^2\right\} - \rho g(h_1 - h_2) = \Delta p_{C1} - \Delta p_{C2}$$

There are a plurality of mathematical models that can be used as curve fitting models for the data obtained from the DRDC viscometer 920, such as a power law model, a Casson model, a Carreau model, a Herschel-Bulkley model, a Powell-Eyring model, a Cross model, Carreau-Yasuda model. It is within the broadest scope of this invention to include all of these models. The following discussion utilizes a power law model and is used by way of example only and not by way of limitation. Thus, one skilled in the art could substitute any of the above curve fitting models for the exemplary power law model discussed below.

The Hagen-Poiseuille flow velocity profile may be used for a Newtonian fluid to derive the following relationship for the capillary pressure loss as a function of capillary geometry, fluid viscosity and flow rate:

$$\Delta p_C = \frac{4\mu L_C \dot{\gamma}}{\phi_C} = \frac{128\mu L_C Q}{\pi \phi_C^4}$$

where the shear rate, $\dot{\gamma}$; is related to the capillary flow rate by $$\dot{\gamma} = \frac{32Q}{\pi \phi_C^3}$$

and, $\Delta p_c$=capillary pressure loss, (Pa);
$\mu$=fluid viscosity, (Kg/ms);
$L_c$=capillary tube length, (m);
Q=volumetric flow rate, (m$^3$/s).
$\phi_c$=capillary diameter, (m).

The above relationship is valid for Newtonian fluids, such as water or mineral oil, for which viscosity is independent of shear rate. For non-Newtonian fluids, the viscosity varies with shear rate. For a fluid that is well-correlated with a non-Newtonian power law viscosity model, the capillary pressure drop can be shown in terms of flow rate using a modified form as follows:

$$\Delta p_C = \frac{4kL_C |\dot{\gamma}|^n}{\phi_C} = \frac{4kL_C}{\phi_C} \left| \left(\frac{3n+1}{n}\right) \cdot \frac{8Q}{\pi \phi_C^3} \right|^n$$

where the shear rate, $\dot{\gamma}$, is related to the capillary flow rate by $$\dot{\gamma} = \left(\frac{3n+1}{n}\right) \cdot \frac{8Q}{\pi \phi_C^3}$$

and the power law viscosity model is written:

$$\mu = k |\dot{\gamma}|^{n-1}$$

Substituting the above relations into the conservation of momentum equation, and neglecting the relatively small inertial terms, a direct equation for obtaining viscosity is derived from the data for Newtonian fluids:

$$\mu = \frac{\rho g (h_1 - h_2)}{32 \left(\frac{\phi_R^2}{\phi_C^4}\right) \left\{ L_{C1} \frac{dh_1}{dt} - L_{C2} \frac{dh_2}{dt} \right\}}$$

The above equation may be used to calculate the fluid viscosity at any time during the test. The data reduction procedure adopted is as follows:

1. Conduct a test and acquire all h(t) data.
2. Fit curves through the data to obtain symbolic expressions for h$_1$(t) and h$_2$(t).
3. Differentiate h(t) with respect to time.
4. Calculate the fluid viscosity and shear rate throughout the data range.

For a non-Newtonian fluid well characterized with a power law viscosity model, the equation becomes:

$$\rho g (h_2 - h_1) = \frac{4kL_{C1}}{\phi_C} \left\{ 2\left(\frac{3n+1}{n}\right) \cdot \left(\frac{\phi_R^2}{\phi_C^3}\right) \left| \frac{dh_1}{dt} \right| \right\}^n - \frac{4kL_{C2}}{\phi_C} \left\{ 2\left(\frac{3n+1}{n}\right) \cdot \left(\frac{\phi_R^2}{\phi_C^3}\right) \left| \frac{dh_2}{dt} \right| \right\}^n$$

Data reduction in this case is complicated by the fact that there are two unknowns associated with the fluid viscosity, k and n. The following procedure is used:

1. Conduct a test and acquire all h(t) data.
2. Fit curves through the data to obtain symbolic expressions for h$_1$(t) and h$_2$(t).
3. Differentiate h(t) with respect to time.
4. Estimate values for the power law parameters, k and n.
5. Calculate the following error values for all data points:

$$\text{Error} = \left| \rho g (h_2 - h_1) - \frac{4kL_{C1}}{\phi_C} \left\{ 2\left(\frac{3n+1}{n}\right) \cdot \left(\frac{\phi_R^2}{\phi_C^3}\right) \left| \frac{dh_1}{dt} \right| \right\}^n + \frac{4kL_{C2}}{\phi_C} \left\{ 2\left(\frac{3n+1}{n}\right) \cdot \left(\frac{\phi_R^2}{\phi_C^3}\right) \left| \frac{dh_2}{dt} \right| \right\}^n \right|$$

6. Sum the error values for all data points.
7. Iterate to determine the values of k and n that minimize the error sum.
8. Use the determined k and n values found in the following equations to determine the viscosity and shear rate range over which the test was conducted:

$$\dot{\gamma} = \left(\frac{3n+1}{n}\right) \cdot \frac{8Q}{\pi \phi_C^3};$$

and $$\mu = k |\dot{\gamma}|^{n-1}.$$

FIG. 11A depicts a graphical representation of the viscosity of a non-Newtonian fluid, e.g., the circulating blood of a living being, versus a range of shear rates and FIG. 11B depicts a logarithmic depiction of the viscosity versus shear rate. It should be understood that the curves depicted in those graphs are identical mathematically and that the DRDC viscometer 920 disclosed above ensures greater accuracy than existing technology.

It should be understood that the MSSS 953 has many other applications outside the viscosity determination art and that its use is not limited to viscosity determinations.

Without further elaboration, the foregoing will so fully illustrate our invention and others may, by applying current or future knowledge, readily adapt the same for use under various conditions of service.

We claim:

1. An apparatus for monitoring the level of a plurality of columns of fluid in a respective plurality of transparent containers substantially simultaneously, said apparatus comprising:
    an optical source of light for each one of said plurality of columns of fluid, each of said optical sources emitting a respective light ray at its corresponding transparent container; and a single detector for detecting at least a portion of each respective light ray that impinges on said corresponding transparent container substantially simultaneously.

2. The apparatus of claim 1 wherein each of said optical sources of light are activated in alternation.

3. The apparatus of claim 2 wherein said detector comprises a charge coupled device (CCD) array.

4. The apparatus of claim 3 wherein said CCD array comprises a refresh rate and wherein said alternated activation is approximately equal to said refresh rate.

5. The apparatus of claim 2 wherein a lens collimator is positioned between each optical source and its corresponding transparent container.

6. The apparatus of claim 5 wherein each of said optical sources comprises a laser.

7. The apparatus of claim 1 wherein said at least a portion of each respective light ray comprises that portion of said light ray that does not encounter the column of fluid in said respective transparent container.

8. The apparatus of claim 1 wherein each of said transparent containers comprises a cylindrical tube.

9. The apparatus of claim 8 wherein each of said cylindrical tubes along with a calibrating fluid having an index of refraction disposed therein refracts its respective light ray towards said single detector.

10. The apparatus of claim 9 wherein said column of fluid comprises an index of refraction different from said calibrating fluid index of refraction which diverts said impinging light ray away from said single detector.

11. The apparatus of claim 10 wherein said calibrating fluid comprises air.

12. A method for monitoring the level of a plurality of columns of fluid in a respective plurality of transparent containers, said method comprising the steps of:

(a) directing a respective ray of light at its corresponding transparent container; and (b) detecting at least a portion of each of said respective light rays that impinges upon said transparent container, said at least a portion of each of said respective light rays that are detected comprising that portion of said light rays that does not encounter any fluid in said transparent containers.

13. The method of claim 12 wherein said step of directing a respective ray of light comprises alternately activating a plurality of optical sources corresponding to said plurality of containers.

14. The method of claim 13 wherein said step of detecting at least a portion of each of said respective light rays comprises utilizing a single optical detector for detecting said at least a portion of each of said respective light rays.

15. The method of claim 14 wherein said step of detecting at least a portion of each of said respective light rays comprises the steps of:

(a) utilizing a cylindrical tube for said transparent containers; and (b) positioning said single optical detector such that when any of said respective light rays impinges on its corresponding cylindrical tube when it is contains a calibrating fluid having an index of refraction, said respective light ray is detected by said single optical detector.

16. The method of claim 15 wherein said light rays that encounter fluid, in any one of said plurality of containers, having an index of refraction different from said calibrating fluid index of refraction are refracted away from said single optical detector.

* * * * *